(12) United States Patent
McGrady

(10) Patent No.: US 7,847,970 B1
(45) Date of Patent: Dec. 7, 2010

(54) SYSTEM AND METHOD FOR RECEPTION, ANALYSIS, AND ANNOTATION OF PRESCRIPTION DATA

(75) Inventor: R. Michael McGrady, Baden, PA (US)

(73) Assignee: AutoMed Technologies, Inc., Chesterbrook, PA (US)

( * ) Notice: Subject to any disclaimer, the term of this patent is extended or adjusted under 35 U.S.C. 154(b) by 1636 days.

(21) Appl. No.: 11/107,962

(22) Filed: Apr. 15, 2005

Related U.S. Application Data

(60) Provisional application No. 60/562,797, filed on Apr. 16, 2004.

(51) Int. Cl.
*G09G 5/00* (2006.01)
*G06F 17/00* (2006.01)
*G06Q 10/00* (2006.01)

(52) U.S. Cl. .............. 358/1.18; 358/403; 358/1.1; 358/1.15; 705/2; 705/3; 715/230; 715/231; 715/233; 715/235; 345/179; 345/581; 345/634

(58) Field of Classification Search .............. 358/1.1, 358/1.15, 402, 403, 527; 382/115; 705/2, 705/3; 715/203, 231, 233, 235, 512; 345/179, 345/581, 634
See application file for complete search history.

(56) References Cited

U.S. PATENT DOCUMENTS

| | | | |
|---|---|---|---|
| 6,551,357 B1 * | 4/2003 | Madduri | 715/235 |
| 7,355,633 B2 * | 4/2008 | Kurosawa et al. | 348/211.8 |
| 7,453,472 B2 * | 11/2008 | Goede et al. | 345/634 |
| 7,493,263 B2 * | 2/2009 | Helmus et al. | 705/2 |
| 2003/0225595 A1 * | 12/2003 | Helmus et al. | 705/2 |
| 2004/0019794 A1 * | 1/2004 | Moradi et al. | 713/185 |
| 2004/0021685 A1 * | 2/2004 | Denoue et al. | 345/721 |
| 2004/0080625 A1 * | 4/2004 | Kurosawa et al. | 348/211.99 |
| 2004/0212823 A1 * | 10/2004 | Chavers et al. | 358/1.15 |
| 2005/0088668 A1 * | 4/2005 | Sesek et al. | 358/1.1 |
| 2005/0177783 A1 * | 8/2005 | Agrawala et al. | 715/512 |
| 2006/0107297 A1 * | 5/2006 | Toyama et al. | 725/105 |
| 2008/0276008 A1 * | 11/2008 | Leon | 705/2 |
| 2009/0164244 A1 * | 6/2009 | Helmus et al. | 705/2 |
| 2009/0164254 A1 * | 6/2009 | Helmus et al. | 705/2 |
| 2009/0222289 A1 * | 9/2009 | Helmus et al. | 705/2 |
| 2009/0309893 A1 * | 12/2009 | Boothroyd et al. | 345/581 |

* cited by examiner

*Primary Examiner*—Kimberly A Williams
(74) *Attorney, Agent, or Firm*—Ralph E. Jocke; Brett A. Schenck; Walker & Jocke

(57) ABSTRACT

An exemplary medication order processing system (10) includes a plurality of nursing stations (12, 14, 16). Physician orders prescribing medications for patients are faxed from the nursing stations to a computer which is included in an interchange fax station (28) located at the pharmacy. Physician orders for medications are selectively sent to either a priority or normal fax number based on the urgency associated with delivering the medication to the patient. The interchange fax station is operative to prioritize the orders and to present them to pharmacists working at pharmacist work stations (40, 42). Pharmacist work stations are enabled to review, electronically annotate, and input orders reviewed at the pharmacy work station into a pharmacy order system of the facility. Input to the pharmacy order system results in the medication being administered to the patient. Pharmacists are also enabled to handle discrepancies and to present issues to the originators of the orders so as to resolve questions before the input of the medication order into the pharmacy order system.

20 Claims, 17 Drawing Sheets

PHYSICIAN ORDER FORM

Title: THIS IS A VALID PHYSICIANS ORDER FORM
PLEASE FILE IN CHART

Physician Name: Dr. Bones
Patient Name: James T. Kirk
Patient ID/MRN: 123-45-6789
Visit Number: 987654
Date of Birth: 02/23/1945
Gender: Male

Hospital: Southwest General Health Center
18697 Bagley Road
Middleburg Heights, Ohio 44130

DC: Actonel — 126

Give: Fosamax 10mg PO Daily — 128
(for current hospitalization only) (transcribe on Kardex)

Notes: This is a sample of therapeutic substitution. — 130

(Per Pharmacy/Pathology/Infection Control Committee Protocol)

PHARMACIST: Rmm — 132

[Clear]

134 — [Send]   [Complete]   [Cancel]   136

SYSTEM AND METHOD FOR RECEPTION, ANALYSIS, AND ANNOTATION OF PRESCRIPTION DATA

CROSS REFERENCE TO RELATED APPLICATION

This application claims the benefit of U.S. Provisional Application No. 60/562,797 filed Apr. 16, 2004, and the disclosure thereof is incorporated herein by reference.

TECHNICAL FIELD

This invention relates to systems for providing medications. Specifically this invention relates to systems and methods that facilitate the processing of physician orders for medications by pharmacists.

BACKGROUND OF THE INVENTION

While physicians prescribe medications for patients, pharmacists have responsibility for preparing the medication for delivery to the patient. Once the pharmacist has prepared the medication it may be administered by a medical professional such as a doctor or a nurse.

In hospitals and other medical facilities one or more pharmacy operations are responsible for reviewing the orders by physicians for medications to be given to patients. The pharmacists then prepare or otherwise make the medication available for administration to the patient. Such requirements can present considerable challenges for pharmacists. There can be difficulties associated with making sure that physician orders, which may include prescriptions for drug medications, are proper. Further, physician orders may need to be retained so that they can be recovered in the event of future questions or a need to further analyze the patient's condition. Thus, there exists a need for improved pharmacy systems and methods for handling physician medical orders.

DISCLOSURE OF INVENTION

In a large medical facility, such as a hospital, pharmacists can receive physician orders from a plurality of nursing stations within the medical facility. One way in which the pharmacy operation can receive such physician medical orders from the nursing stations is via facsimile (fax) transmission. A physician medical order which requests a particular medication for a patient can be prepared in an area adjacent to a nursing station. The medical order can include information concerning the patient, the patient's location within the facility, patient condition, and/or other information pertinent to the use of medication by the patient. This information can be presented in a structured format such as on a form. The form can be signed by the prescribing physician.

The medication order can then be faxed from a fax machine/computer at the nursing station to a fax machine/computer in the pharmacy, where the faxed orders can be reviewed by a pharmacist. The pharmacist can analyze the information on a physician medical order and, if no issues or concerns are noted, then the pharmacist can have the physician medical order information entered into the pharmacy system or other entry system. Such entry can cause the records associated with the patient to indicate that the medication is to be administered to the patient. This entry can cause an electronic medication order for the patient to be established in the hospital's pharmacy system. The electronic medication order may indicate the medication as well as the dosage, frequency, method of administration, and other information pertinent to providing the medication to the patient. This administration may be done, for example, through a system which provides for the dispensing of medical items from automated dispensers in response to inputs from nurses or other medical professionals in the vicinity of the patient.

In other situations the entry of physician medical order information into the pharmacy system by the pharmacist may cause actions to be taken. These may include, for example, specially preparing the medication for the patient and arranging to have it delivered to the area of a hospital where it is needed.

In some institutional environments medications may be needed immediately, or on a "stat" basis. To handle these orders more rapidly, provision can be made for a separate fax machine/computer in the pharmacy specifically designated for receiving physician orders which have an urgent priority. Physician orders can be sent to this high-priority fax receiving machine by nurses or other medical professionals by dialing the phone number or extension number associated with this stat fax receiving machine rather than the regular fax receiving machine in the pharmacy. Orders received through the designated high-priority fax receiving machine for urgent orders can be given priority by the pharmacists entering them into the pharmacy order system or other system.

Pharmacists may sometimes have questions or issues with regard to physician orders that are received. For example, pharmacists may uncover situations where orders are incomplete or inconsistent. This may require the pharmacy to request further information from the doctor or other professional that submitted the order. Pharmacists may communicate to the originating point of the order by return fax to try to clarify inconsistencies or to obtain needed information. Such faxed clarifications can be requested in writing so as to avoid any misunderstandings.

Pharmacists may also have other issues or concerns regarding received physician orders, such as possible adverse interactions between medications that have already been prescribed for the patient and a newly prescribed medication. In such cases the pharmacists may put the order on "hold" pending the receipt of further clarifying information. Likewise, a pharmacist may determine that a prescribed medication is a duplicate of a medication previously prescribed. Again, in such situations the pharmacist may place the order on hold pending further clarifying information from the originating source. Also, a pharmacist may need to substitute a different brand or type of medication for the one that was prescribed in the order. Again, these issues need to be worked out by the pharmacist before the pharmacist inputs the order into the pharmacy order system, and before the medication is administered to the patient.

In an exemplary embodiment of the present invention, pharmacists can ensure that all physician orders are properly entered into the pharmacy system and that urgent orders are given appropriate higher priority. In addition, orders that are waiting for further information before they can be entered can be retained so as not to be lost. Further, all such physician orders can be documented. For example, a copy of a fax which resulted in the entry of a medication order can be retained so that it can be later recovered to answer any future questions relevant thereto.

It is an object of an exemplary embodiment of the present invention to provide an improved system for processing physician orders in a pharmacy.

It is a further object of an exemplary embodiment of the present invention to provide improved methods for processing physician orders.

Further objects of exemplary embodiments of the present invention will be made apparent in the following Best Modes for Carrying Out Invention and the appended claims.

The foregoing objects are accomplished in an exemplary embodiment of the present invention by a system used in a health care facility. The exemplary system includes a plurality of nursing stations. The nursing stations are located in the various wards or other areas of the medical facility where patients are treated. Each nursing station includes a fax machine or other image transfer device for transmitting images of medication orders to a pharmacy.

Communication lines extend between the nursing stations and one or more computers located in the pharmacy. A computer located in the pharmacy is operative to receive the data which comprises faxed physician orders that are sent both with normal priority as well as with a high priority.

The computer in the pharmacy that receives the faxed orders is in operative connection with one or more pharmacist work stations. The computer which receives the faxes is operative to prioritize the incoming faxes based on priority and time received, and to present an electronic representation of each order to the pharmacist work stations. Each pharmacist working at a pharmacist work station is automatically presented with the next order in a queue based on time received and priority. In the exemplary embodiment the orders are presented on a screen in a full sized visual representation. The pharmacist is also presented with a screen which includes a number of options for functions which can be performed as well as a listing of the pending physician orders in the queue that are waiting to be addressed. In the exemplary embodiment, orders at a top area of the queue have a higher priority than orders at a bottom area of the queue. Of course it should be understood that other queue ordering arrangements may be used.

In the exemplary embodiment the pharmacist work station is operative to automatically locate and enlarge on a first screen a defined quadrant of the order image to more clearly present the patient name and other identifying data to the pharmacist. Upon seeing the patient name and ID number or other data, the pharmacist is enabled to provide inputs to the pharmacist work station which brings up information about the patient on a second screen associated with the pharmacist work station. The pharmacist then may provide an input that causes the defined quadrant to no longer be enlarged. The pharmacist may review the information in the order and take actions such as to enter data corresponding to the order into the pharmacy order system, or place the order on hold for a period of time pending receipt of further information. In some exemplary embodiments the pharmacist may operate the pharmacist work station to place annotations or questions on the order and/or to cause an image of the order to be faxed back to the originating nursing station with a request for information. Further, in an exemplary embodiment the pharmacist may add additional annotations or markings of a predefined or customized type to the image. This may be stored in a database in correlated relation with the image data corresponding to the order to facilitate accurate record keeping related to the image information.

In the exemplary embodiment the actions of the pharmacist in accessing patient data through the pharmacy system also causes data provided from that system, such as patient name, patient ID, date of birth or other defined data, to be included or correlated with the image data related to the order. Once the pharmacist has completed the entry of the order into the pharmacy order system, the image and the annotations made by the pharmacist are saved in one or more data stores and the electronic representation of the next order is presented to the pharmacist.

It should be understood that these approaches are exemplary and in other embodiments other approaches may be used.

DESCRIPTION OF DRAWINGS

FIG. 8 is an example of an order that has been marked using the various tools for marking the order provided by the pharmacist work station.

FIG. 14 is an output screen from a pharmacist work station associated with a tool for searching for a particular faxed order.

FIG. 17 is a substitution order form generated by the exemplary pharmacist workstation.

FIG. 21 is an exemplary output screen for configuring the size of notes and stamps that are applied to physician order images.

BEST MODE FOR CARRYING OUT INVENTION

Figure 1:
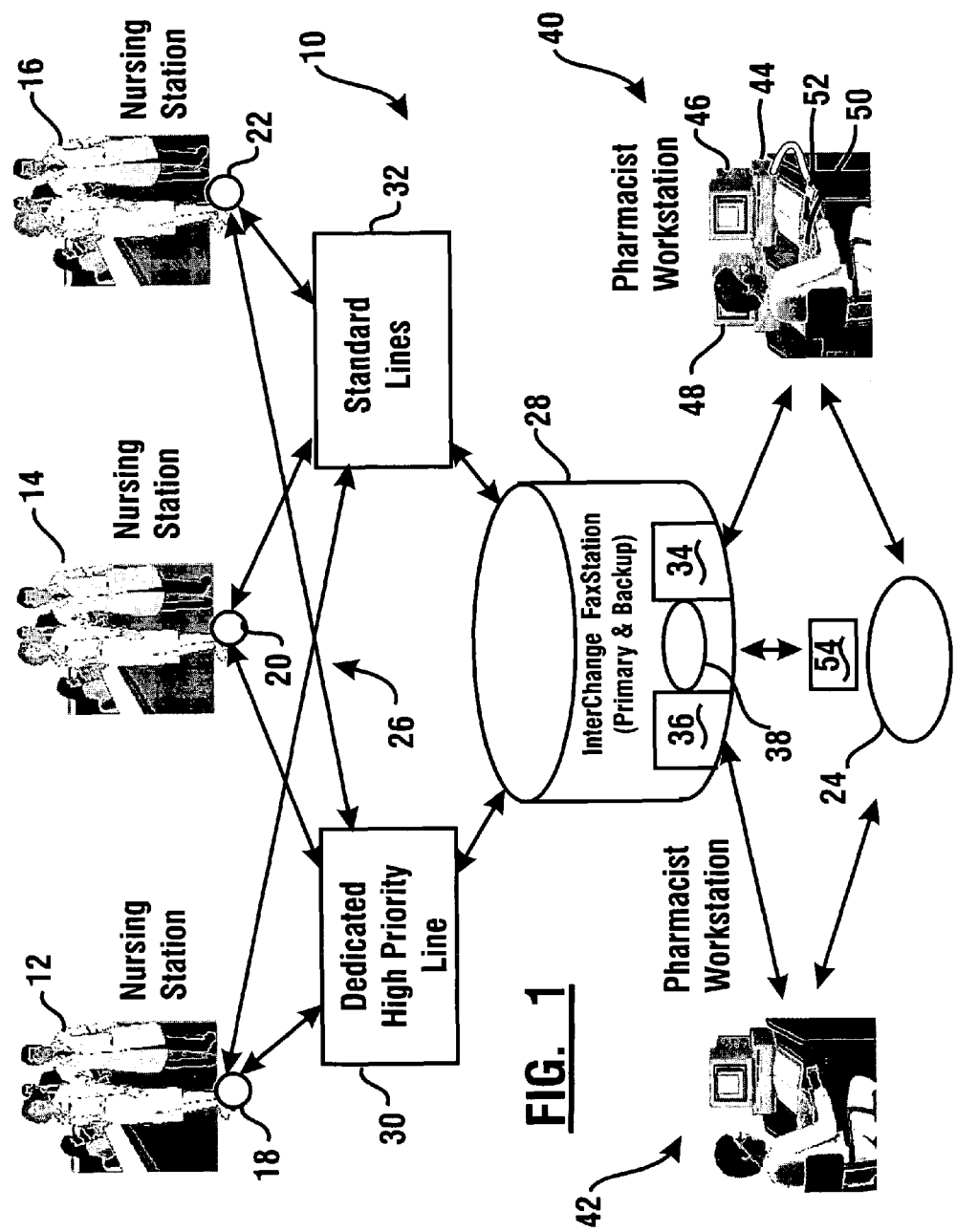
FIG. 1 is a schematic view of a system for processing medication orders.

Referring now to the drawings and particularly to FIG. 1, there is shown therein an exemplary system 10 for processing physician orders for medications to be administered to patients. The exemplary system includes a number of medical stations 12, 14, 16, such as nursing stations. Each nursing station or post is generally located adjacent to wards or rooms where patients may be housed within a hospital or other care facility. Each nursing station generally includes a fax machine or other imaging device 18, 20, 22 which can be used to image a physician order which has been signed or otherwise authorized by a physician and which is to be transmitted to the pharmacy for entry into a pharmacy order system 24 so that the medication can be administered to the patient.

In alternative arrangements, the nursing stations can include computers that can communicate with the pharmacy via Internet transmission communication instead of or in addition to fax transmission communication. A nursing station computer may comprise software enabling input to a medical order form via a keyboard and/or a touch screen. The nursing station computer may also include a signature pad enabling entry of a physician signature on the medical order form therewith. The signed form can then be transmitted to a pharmacy number or a pharmacy Internet address via fax or the Internet. In further arrangements, a nurse may have a hand-held device with a processor that allows completion of a medical order form and input of a physician's signature. Thus, a nurse can fill out a physician medical order and obtain the authorizing physician's signature while away from their nurses station. Wireless communication can also be used to transmit a physician medical order to a pharmacy. A physician medical order may be transmitted wirelessly from either the nurse's station or the nurse's hand-held device. The nurse's hand-held device may also wirelessly download information therefrom to the nurse's station.

As represented in FIG. 1, a physician medical order transmitting device (e.g., fax machine) at each nursing station is enabled to communicate through phone lines, network or other communication system 26 with one or more computers that are located in the pharmacy. These one or more computers are referred to as an interchange station 28. The interchange station 28 includes one or more processors and data stores suitable for processing and storing instructions and information.

In an exemplary embodiment the interchange station is an interchange fax station. The interchange fax station computers can automate the reception, queuing, and storage of physician medical orders that are received from nursing stations and/or other points within a health care facility. In the exemplary embodiment, fax reception is supported on multiple phone lines. These phone lines include at least one designated line 30 for urgent or "stat" handling as well as at least one line 32 for normal handling. The interchange fax station 28 of the exemplary embodiment is enabled to be in communication with multiple lines for receiving stat orders as well as multiple lines for receiving normal (non urgent) orders. For example, station 28 can comprise a computer station including at least two phone lines, each line assigned a different handling priority. The fax handling priority can be based on which of the two phone lines received the medication order.

The interchange fax station 28 of the exemplary embodiment is operative to receive fax data corresponding to images of physician orders and to automatically place the images in storage in a relational database. The images (or data representative of the images) can be placed in the appropriate stat or normal queue based on the fax line on which the fax was received. The interchange fax station, if necessary, is also operative, in accordance with its programming, to conduct image processing on received orders, such as the decoding of received faxes, converting the faxes to compressed electronic image format, and storing the electronic images in the database. The exemplary interchange fax station is also operative to continue to store orders that are entered, processed, or deleted until a configurable time limit is reached. Upon expiration of this time limit they are permanently removed from the database.

Exemplary forms of the interchange fax station may also operate in accordance with their programming to manipulate the data corresponding to order images to improve clarity. This may be accomplished, for example, by changing pixel values for pixels in the images to provide greater contrast between light and dark pixels. Alternatively, image data may be manipulated to be aligned with an imposed coordinate system by the computer to compensate for any skewing of the order as it moved in the fax machine. Other types of image data manipulation may be provided in accordance with the programming of the computer software of the interchange fax station.

In the exemplary embodiment the interchange fax station 28 includes a primary computer 34 and a backup computer 36 that are physically connected via an Ethernet hub 38. The primary computer 34 includes mirrored hot swappable disk drives while the backup computer is generally maintained without drives. This enables the backup computer to be made the primary computer by swapping the disk drives. Thus the backup computer may become the primary computer without touching any network cables or other connections. Further in the exemplary embodiment both the primary and backup computers are connected to a power source through an uninterruptible power supply.

In the exemplary embodiment the interchange fax station 28 is in operative communication with one or more pharmacist work stations 40, 42. The pharmacist work stations 40, 42 comprise computers at which pharmacists can operate to review medication orders. The pharmacy system, in an exemplary embodiment, is operative to enable pharmacists to automate the process of converting physician medication orders on paper into electronic medication orders within the pharmacy system 24. In an exemplary arrangement the work stations are connected via a network (intranet and/or Internet) and allow users thereof to communicate with each other, such as by electronic messages (e-mail, instant messaging, etc.).

In an exemplary embodiment, a pharmacist work station includes a computer 44 with dual output display screens 46, 48, a keyboard 50 and a mouse 52. The pharmacist work station can be operated in accordance with the programming of computer software therefor. The screens or "monitors" 46, 48 are preferably sized to be able to display electronic representations of physician medication orders at full size. The exemplary pharmacist station includes a single keyboard and mouse that can operate and provide inputs through graphical user interfaces output through both display screens 46, 48 without the need for a switch or other signal directing device. In an exemplary embodiment, one display screen is used by a pharmacist to review physician orders requesting medication and the other display screen is used by the same pharmacist to enter approved medication orders into the pharmacy order system. In other embodiments a pharmacist work station can have more than two display screens.

The exemplary pharmacist work station 40 includes output display screens with touch screen capability. The touch screen may act as a mouse and provide a fast user-friendly way to annotate an electronic representation of a physician order by touching the screen. In the exemplary embodiment the pharmacist work station 40 is also operative to output an audible tone through a speaker or other audio output device to indicate if the screen has been touched.

Further, in the exemplary embodiment, input devices such as the keyboard, touch screen, and/or mouse can be used to add annotations (e.g., notes, checkmarks, highlighting, and other indicators) to the electronic representation of the image. This facilitates the ability of a pharmacist to annotate a displayed image of a physician medication order with pharmacist-added information, such as comments or questions.

Further, in the exemplary embodiment, the pharmacist work station is operative to capture data regarding the patient such as the patient ID, name, date of birth, gender, ward/room location, and/or other information from the pharmacy order entry system and to incorporate that information into displayed image data and in the relational database. This is done in the exemplary embodiment through use of a software "screen scraper" operating in the computer 44 which captures a graphic representation of the information from selected parts of visible outputs provided from the pharmacy order system. For example, a first one of the dual display screens can show patient (identifying) data from the pharmacy order system. This displayed patient data (or a portion thereof) can be captured and then copied into an electronic image of a physician medical order (from the medication order system) displayed on the second of the dual display screens. Capturing this (patient data) information in the medical order image data helps to verify that the order was entered for the appropriate patient. The electronic image of the physician medical order containing the added patient data can then be stored. A work station enables data from a pharmacy order system to be analyzed on one display monitor, captured therefrom, inserted for display (along with a medication order) on a display monitor of a medication order system, and saved in the medication order system. Hence, data can be captured/copied from the pharmacy order system to the medication order system, and vice versa. Of course it should be understood that the pharmacy order system comprises a network including one or more connected computers which operate to include medication orders in the stored data associated with the patient that helps to assure that the medication ordered for the patient by the physician is administered.

In the exemplary embodiment the pharmacist work station 40 is programmed to provide numerous useful functions. These include prioritizing the physician orders so that they are handled in a priority order. In the exemplary embodiment, orders are prioritized based on when they are received as well as whether they have stat or normal priority. When pharmacists first log in to a pharmacist work station and after the handling of each order is completed, or otherwise disposed of by being discarded or placed on hold, the pharmacist work station through interaction with the interchange fax station operates in accordance with its programming automatically to select the next fax physician order that has the highest priority for processing. Of course, as is later apparent, in the exemplary embodiment a pharmacist may optionally select any fax physician order to review by inputs to their pharmacist work station.

In the exemplary embodiment the pharmacist work station 42 may be programmed to operate in connection with the interchange fax station 28 so as to selectively direct particular orders for processing. For example, the system may be configured so that a particular pharmacist may review and process all orders. Alternatively the system may be configured so that certain faxes are assigned to specific pharmacists, or to a separate pharmacy operation within the pharmacy facility. This may be accomplished through programming of the interchange fax station 28 and pharmacist work station. For example, faxes may be directed based on certain criteria such as the fax machine from which the order originated, the communication line that received the fax order, the type/amount of medication requested, the location of the patient, the availability of the pharmacist, or other criteria. In other embodiments the functions of fax station 28 and the functions of a pharmacist work station may be combined to operate as a single integral unit.

In an exemplary embodiment, faxed medication orders can be temporarily placed on "hold" by the pharmacist while waiting for clarification. This can be done by an appropriate input by the pharmacist. The pharmacist work station is programmed so that faxes that have been placed on hold are necessarily defined to time out of the hold state and revert back into the appropriate queue for handling. This helps to assure that a fax will not be forgotten if it is placed in a hold state.

In an exemplary embodiment the programming of the pharmacist work station includes an automatic zoom feature. In an exemplary embodiment this feature automatically zooms in on and enlarges a defined quadrant of the fax image when the image is first displayed on a display screen of the work station. This may be useful with regard to order forms where necessary patient information and ID numbers are needed for purposes of queuing up corresponding information in the pharmacy order system may be small or otherwise difficult to read. Further in an exemplary embodiment fax images are enabled to be selectively zoomed, panned and rotated through inputs to the pharmacist work station. Further, in alternative embodiments, characters in the selected quadrant may be analyzed by character recognition software to resolve patient name and ID data. The pharmacist work station may output this data to the pharmacy system which automatically causes the pharmacy data corresponding to the patient to be output. In such embodiments the pharmacist need only verify the accuracy of the analysis by reviewing the screens rather than providing manual inputs to bring up the patient data from the pharmacy system.

In the exemplary embodiment the pharmacist work station has included in its programming certain electronic image annotation tools. These annotation tools include the ability to provide checkmarks, highlighting, electronic ink, notes and stamps to allow the pharmacist to annotate the electronic image as they perform their work.

In an exemplary embodiment the pharmacist work station 40 in conjunction with the interchange fax station 28 is programmed to provide a fax-back function. The fax-back function allows pharmacists to quickly return a fax to the sending nursing station (or other location) for clarification. For example, human-readable (typed or written or predefined) comments or questions added to a physician medication order at a pharmacy can be faxed-back to a nursing station for reading by a nurse. Alternatively faxes may be sent by the pharmacist through inputs to their work station to another fax machine such as a machine located in a physician's office. This enables the pharmacist to receive the clarifying information necessary to enter the order more rapidly and in a documented manner.

The exemplary pharmacist work station 40 further provides therapeutic substitution capability. This feature enables the pharmacist to quickly choose a predefined substitute medication or medication property or aspect, such as the form, dose or strength. Such predefined therapeutic substitutions may be set by hospital policy through predefined tables and rules which are stored in connection with the pharmacist work station.

Further features of the exemplary embodiment of the pharmacist work station include security features. These features may include, for example, user ID card or combined card and PIN access to assure that the pharmacist work station can only be accessed by an authorized user. Further, exemplary embodiments impose a periodic mandatory PIN change to minimize the risk that a pharmacist's personal login information may be stolen by unauthorized persons. A further aspect of an exemplary embodiment provides for a user to be automatically logged out of the terminal if they do not provide inputs within a preset time. This avoids the risk that a user will leave a terminal in an unattended condition such that it can be accessed by unauthorized persons.

The exemplary embodiments also provide an audit trail of information that has been input to the system. In addition, because the interchange fax station captures patient information directly from the pharmacy order system and stores it in conjunction with the corresponding medication order from the physician, the order data can be searched and analyzed using the information that is derived from the pharmacy order system. This facilitates recovering information that is stored in the system. Of course these approaches are exemplary and in other embodiments other or additional features may be included.

In an exemplary embodiment, reviewer work stations 54 may be provided. Reviewer work stations 54 may be similar to pharmacist work stations 40 except with more limited functionality. In an exemplary embodiment, medication orders cannot be entered into the pharmacy order system through reviewer work stations 54. However, the stations 54 can enable a user to review electronic representations of faxes and annotations regarding physician orders represented by data stored in the interchange fax station computers and/or in other data stores. The exemplary reviewer work stations 54 also provide the ability to change the priority status of physician medication orders. For example, a reviewer work station can be used to raise the status of a particular physician order from normal to stat. The exemplary reviewer work stations 54 also provide the ability to annotate an electronic image of a physician medication order. For example, a reviewer work station can be used by an assistant to annotate a new order to indicate that a first level of review was completed and by whom. If an obvious error was noted in the review then the order can be faxed back to the originating medical station along with annotation questions to resolve the error. A first level of review can reduce pharmacist review time. Also, a reviewer work station can be used to further annotate a previously annotated physician medication order.

In an exemplary embodiment the interchange reviewer work station 54 may be configured to review all orders or selected orders within the pharmacy. For example, a reviewer work station may be configured to review orders that are being handled in a particular pharmacy location. Alternatively reviewer work stations may be configured to monitor orders which are coming from particular nursing stations, fax or other imaging machines or groups of devices, either inside or outside the facility. This enables a reviewer to monitor various types of information as appropriate to carry out their functions.

In the exemplary embodiment the interchange reviewer work station 54 may also be operative responsive to user inputs to zoom, pan, and rotate fax images. Further a reviewer at a reviewer work station 54 can provide markings such as checkmarks, highlighting, electronic ink, notes, and stamps so that they can annotate images as they wish. In addition the reviewer work stations in the exemplary embodiment are enabled to conduct searches based on data that has been stored in image data and that was captured from the pharmacy order system. The reviewer work stations 54 may also include security features and audit capabilities similar to those provided for pharmacist work stations. Of course these approaches are exemplary and in other embodiments reviewer stations may be provided which have different or other types of functions. Furthermore, pharmacist work stations and reviewer work stations may be located in satellite offices which are part of the pharmacy or pharmacy arrangement. As previously discussed, work stations (i.e., pharmacist and reviewer work stations) can be connected to the same network (e.g., intranet and/or Internet) allowing the pharmacy arrangement to have work stations remotely located relative to each other. For example, one or more pharmacists may be situated in the pharmacy arrangement at a geographic location that is remotely disposed from the reviewers' geographic location.

Figure 2:
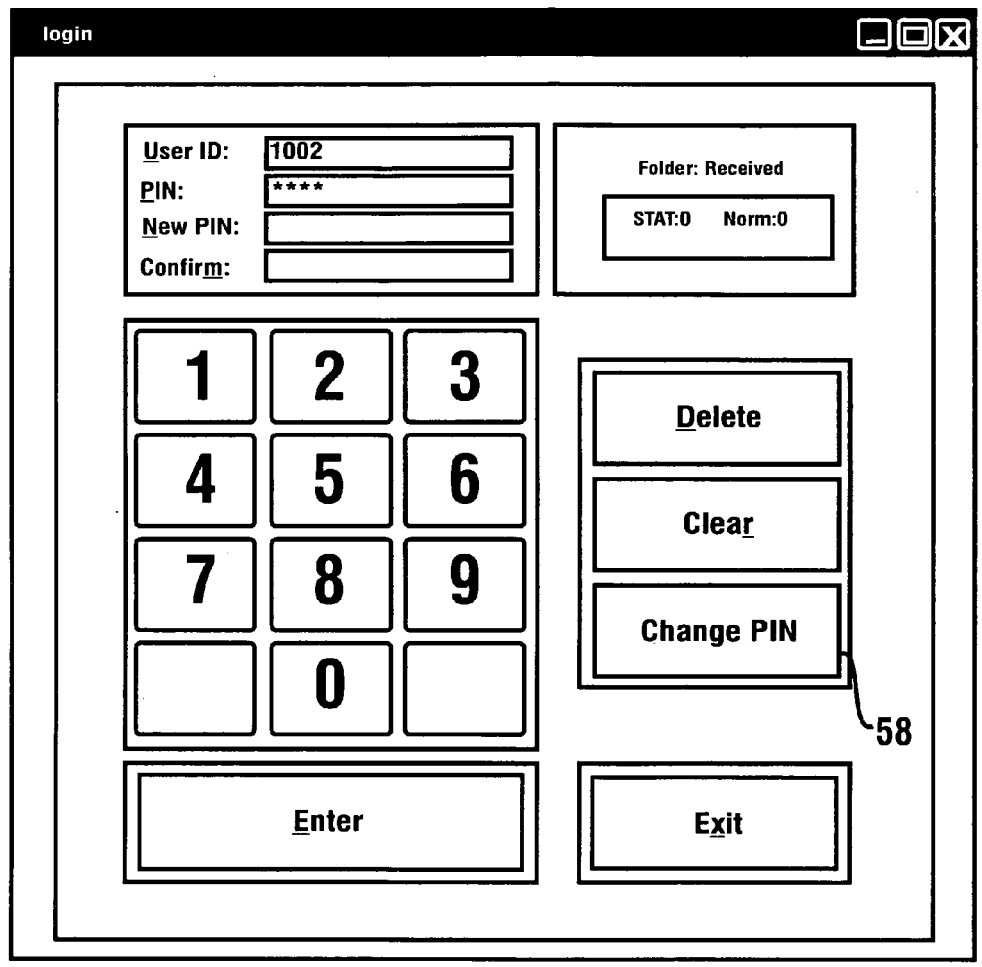
FIG. 2 is an exemplary login screen at the pharmacist work station.

FIG. 2 shows an exemplary embodiment of a login screen 56 that is produced by the pharmacist work station. A pharmacist is required to provide information through inputs responsive to this screen before being able to access the functions available through the pharmacist terminal. Further as previously discussed, reviewer work stations 54 may also incorporate similar features. In the exemplary embodiment, a pharmacist is required to provide both a user ID and PIN in order to gain access to the system. Of course as previously discussed, in some embodiments the user may be required to provide data which is included on a card which is read by a card reader or similar device that is in operative connection with the pharmacy terminal. As indicated in FIG. 2 an icon 58 is provided for a user to change their PIN. If a user selects this option after entering the correct PIN they may input a substitute PIN. The substitute PIN may be used by them thereafter for purposes of accessing the system. In some exemplary embodiments the pharmacist work station is programmed so that the user is required to change their PIN periodically within a set number of days. If the user fails to make such a change in a timely manner they may be prompted through an output from the work station after logging in to do so and prevented from accessing further functions until a PIN change is input. Of course these approaches are exemplary.

Figure 3:
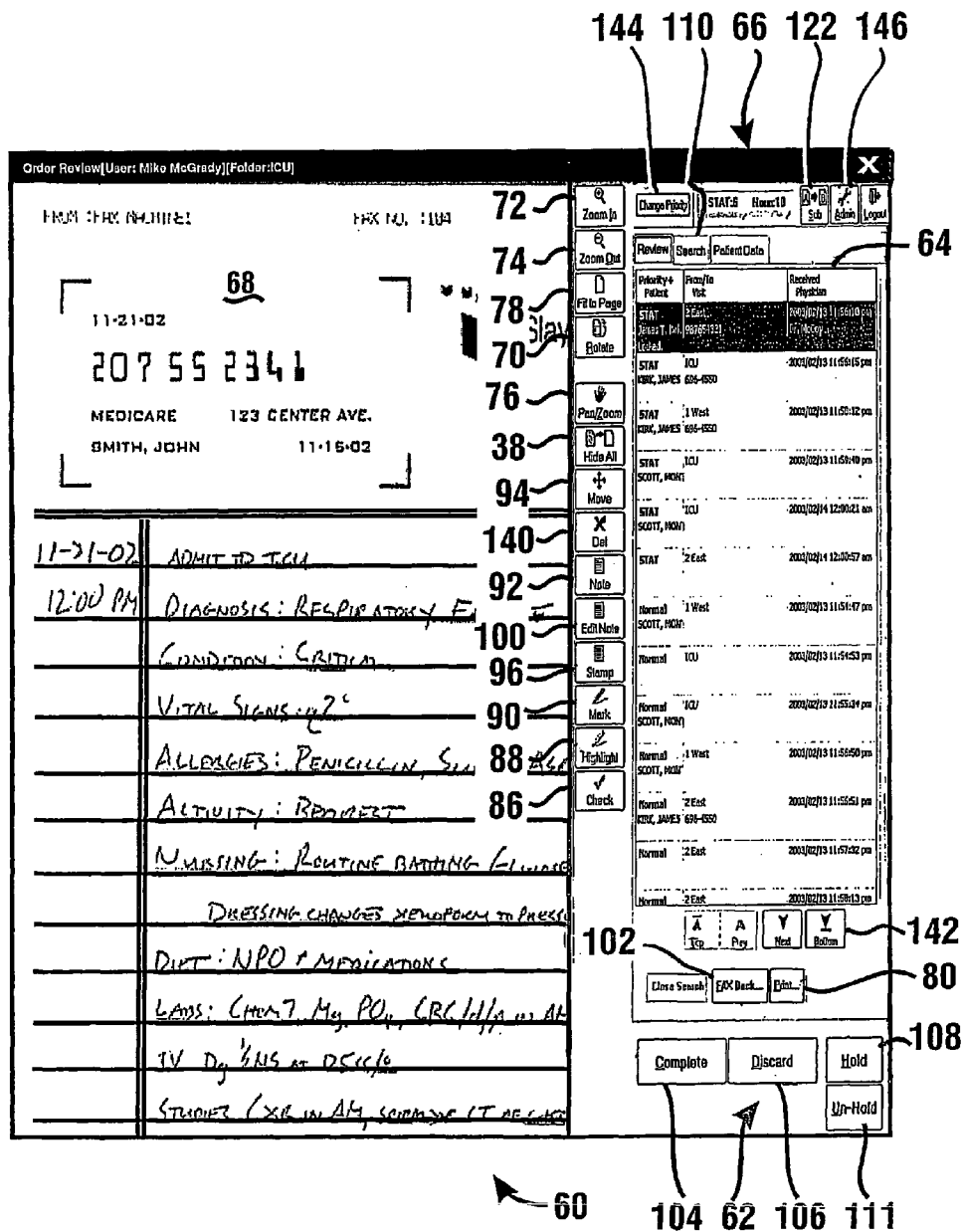
FIG. 3 is an exemplary view of a medication order presented on a screen of a pharmacist work station.

In an exemplary embodiment, once a pharmacist has logged into the pharmacist work station successfully, the pharmacist is presented through a display screen an order review browser interface 60 shown in FIG. 3. As discussed in more detail later, a review button 120 may be used to place the display screen back in the format shown in FIG. 3. The format of the exemplary physician order review interface screen shown in FIG. 3 includes the displaying of at least a portion of an electronic image corresponding to a received physician medical order. Through the order review interface 60, a pharmacist is able to browse through and review electronic images corresponding to the physician orders. Controls that are accessible through the order review interface 60 enable the pharmacist to rotate, zoom in or out, scroll, and pan the electronic representation of the faxed physician order. The controls also enable the pharmacist to place annotations, such as markings and/or comments, on the electronic representation of the faxed physician order. These controls can be displayed on the screen, which can have touch screen capability. As previously discussed, work station input devices such as a keyboard, touch screen, and/or mouse can be used to add annotations to an electronic representation of a displayed image. After the pharmacist has reviewed the order it may be indicated as completed, discarded, or placed on hold through the selection of window buttons 62 shown in the order review interface screen.

The format of the exemplary physician order review interface 60 shown in FIG. 3 also includes the displaying of a queue 64 of physician orders in priority ordering or sequencing in a window. Physician orders are automatically ordered in the queue, first by stat priority and then by normal priority based on their time received. Stat orders are ordered in first-in first-out priority order. Likewise, normal orders are ordered in first-in first-out priority order. As shown in FIG. 3, the stat physician orders are prioritized higher in the queue than the normal physician orders. The stat physician orders are arranged by time relative to each other. Likewise, the normal physician orders are arranged by time relative to each other.

The physician orders queue window can indicate the highest priority fax order at the top of the queue. In an exemplary embodiment, when the pharmacist logs on to a pharmacist work station and the work station mode is set to display the queue window, the top priority fax image is automatically selected and displayed on the display screen through operation of the interchange fax station, the pharmacist work station, and the pharmacist work station display device. A work station enables a pharmacist the ability to simultaneously display on the same display screen both a physician medication order along with an order-prioritizing queue containing other awaiting orders. The display of the order queue enables a pharmacist to be aware of a change in medication order filling priorities. For example, assuming there are no stat orders pending, if a stat order then comes in while the pharmacist is reviewing non-stat order, the work station enables the pharmacist to note the stat order in the queue, stop reviewing the currently displayed (lower priority) non-stat order, handle the stat order, and then return to complete the previously displayed non-stat order. In other arrangements the work station can notify the pharmacist (whether or not the queue is displayed) of a new stat order via a pop-up notification window on the display screen, an audible alarm, a visible alarm (e.g., flashing light), and/or some other notification method.

As represented in FIG. 3 on the right side of the order review interface screen, the queue 64 of pending physician orders is displayed. This area of the output indicates the orders in the queue, and the order being displayed is highlighted. Further as shown in the upper right of the order review interface window, an output indicator 66 is provided to the user showing the numeric number of stat orders and normal orders currently in the queue.

In exemplary embodiments, when the pharmacist logs onto the pharmacist work station the electronic image corresponding to top priority fax 68 is automatically selected and displayed on the left-hand side of a display screen. Further, in exemplary embodiments, the pharmacist work station is programmed to automatically zoom to a selected specific quadrant of the order image and enlarge it on the screen. The pharmacist may choose to process the order that is displayed or may choose to handle another fax from the queue. This is done by highlighting that fax in the listing of orders in the queue 64 presented on the right side of the display. In exemplary embodiments, when multiple pharmacists' work stations are being used, physician orders that have been processed by other pharmacists are displayed in a distinctive color. Once another pharmacist has begun to process the physician order, a pharmacist at the pharmacist work station can review these orders in a read-only mode. The pharmacist work station is programmed so that toolbar options and icons that would otherwise be operative in the user interface when another pharmacist at another work station is handling a particular order, are grayed out and are unable to be selected when the pharmacist is reviewing the order.

In the exemplary embodiment the data in the order queue shown in the order review interface 60 may be sorted by the criteria in the column headings. For example, orders may be displayed by priority from where they originated or from the received physician. By clicking (e.g., via a mouse or keyboard keys) on a column heading the display of the queue orders is automatically reordered. In addition, the data may be selected by either ascending or descending order. The queue priority currently imposed on a display screen is reflected in an exemplary embodiment by the presentation of a plus sign (+) for ascending order or a minus sign (−) for descending order in the column for the criteria which is being used to order the data.

In exemplary embodiments, the area to the right of the physician order 68 shown in FIG. 3 includes icons for tools and controls that can be used by the pharmacist. These tools and controls allow the pharmacist to manipulate or modify the displayed electronic image and to annotate directly in the electronic image.

In the exemplary embodiment a rotate icon 70 is provided. Icons are alternatively referred to herein as buttons. Selection/activation of a displayed rotate icon 70 by clicking on the screen (e.g., via a mouse or keyboard), using voice command, or touching the touch screen at the icon can rotate the physician order image 90 degrees. For example, if the fax is received upside down, clicking the rotate button 70 twice will cause the fax to be displayed right side up.

A zoom in icon 72 is provided. When the zoom in button 72 is selected, the point where the mouse indicator resides on the order image becomes the center of a zoom area. Holding the mouse button on the spot will continue to cause the effect of zooming in on the electronic image until the mouse button is released.

Similarly, a zoom out icon 74 is provided. Selection of the zoom out button 74 makes the image smaller. The point where the mouse is clicked on the image becomes the center of a zoom out area. Holding the mouse button on the spot continues the zoom out effect until the mouse button is released.

In an exemplary embodiment a pan/zoom icon 76 is provided to move the image within the image window. When the pan/zoom button 76 is selected, holding the mouse button down and moving the mouse is operative to cause the image to move. Holding the mouse button down without moving the mouse causes the image to be zoomed in around the spot where the mouse pointer is located. In the exemplary embodiment, after using the rotate, zoom, and pan controls, the image may be restored to full size by touching the fit-to-page button 78. This causes the image to be displayed in full size and in normal perspective within the area of the display screen.

The exemplary embodiment of the pharmacist work station also provides the pharmacist with printing options. In some operations pharmacists will wish to print every fax or in other operations only selected faxes will be printed. In addition, in some situations pharmacists may wish to have faxes printed with all electronic annotations they have included on (added to) the fax image, while in other situations only the original fax as received (or the fax image as originally stored, without annotations) is desired.

Figure 4:
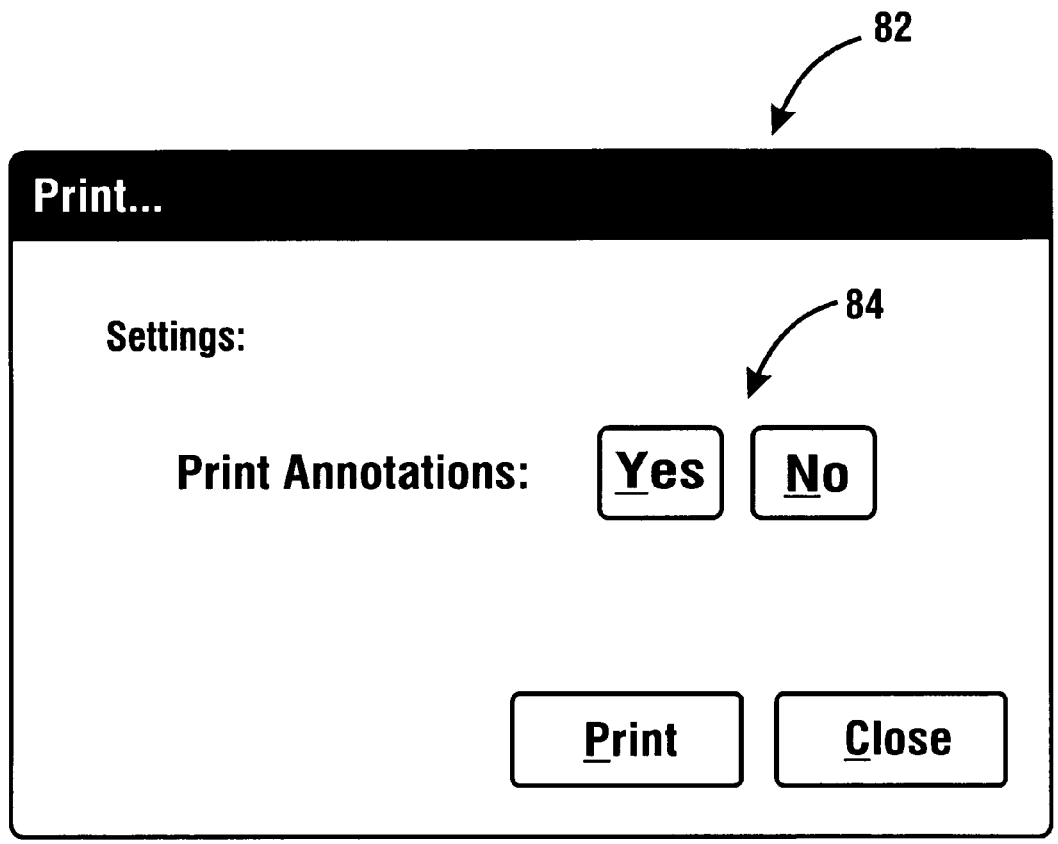
FIG. 4 is an exemplary print window output on a pharmacist work station.

In an exemplary embodiment, the order review interface screen (FIG. 3) includes a print button 80. Selecting the print button causes the print window 82 shown in FIG. 4 to be displayed. The print window 82 has buttons 84 which enable the user to select whether to print the electronic representation of the physician order with or without annotations. Further if the pharmacist has initially chosen to print a physician order but then changes their mind, they may simply choose to close the print window. Of course, as previously discussed, these approaches are exemplary and in some embodiments every order may be printed either with or without annotations based on the programming of the pharmacist terminal, whether the pharmacist chooses to specifically print the order or not.

Figure 5:
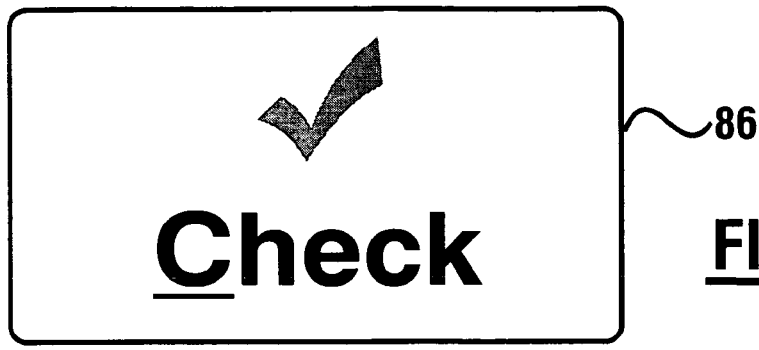
FIG. 5 is an exemplary icon associated with a check tool provided by the pharmacist work station.

In the exemplary embodiment the pharmacist work station enables the pharmacist to utilize electronic image annotation tools which can be used to provide electronic markings in the image data associated with a physician order. As shown in FIG. 3, the order review interface screen includes a check tool icon 86. This icon is shown in further detail in FIG. 5. Clicking on or using the touch screen to select the check tool icon 86 will cause a virtual check mark to appear in the electronic representation of the fax image each time thereafter that the screen is touched until another tool is selected. Checkmarks are shown in the physician order image in FIG. 8.

Figure 6:
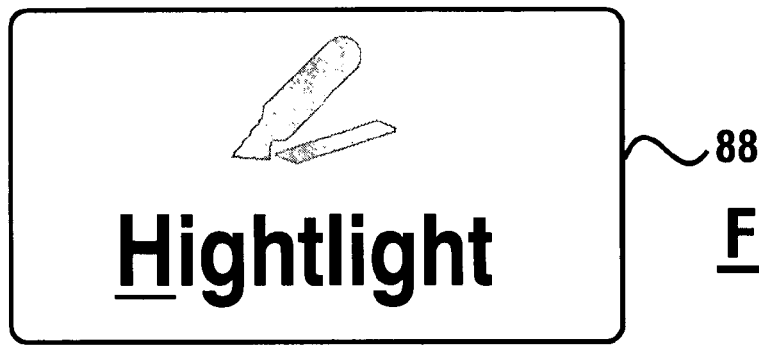
FIG. 6 is an exemplary icon associated with a highlight tool provided by the pharmacist work station.

A highlight tool icon 88 is also available in the order review interface screen, as shown in FIG. 3. The highlight tool icon is shown in more detail in FIG. 6. Selecting the highlight tool icon 88 enables highlighting of portions of a displayed electronic image of a physician order with a virtual color marker. This may be done by a user, such as a pharmacist, moving their finger over the image if there is a touch screen or through use of a mouse. The highlighting function will continue (remain active) in the exemplary embodiment until another tool is selected.

Figure 7:
FIG. 7 is an exemplary icon associated with a marking tool provided through an exemplary pharmacist work station.

The exemplary embodiment also includes a mark tool icon 90 as represented in FIG. 3, and which is shown in more detail in FIG. 7. Selecting the mark tool icon 90 enables a user to virtually write or draw on the electronic representation of a displayed physician order. This enables a user to virtually circle particular portions of text or otherwise provide markings represented on the displayed image either through the mouse or by use of the touch screen. Once the marking tool is selected, touching the screen or moving the mouse will result in further markings appearing on the displayed image until another tool is selected.

Figure 8:
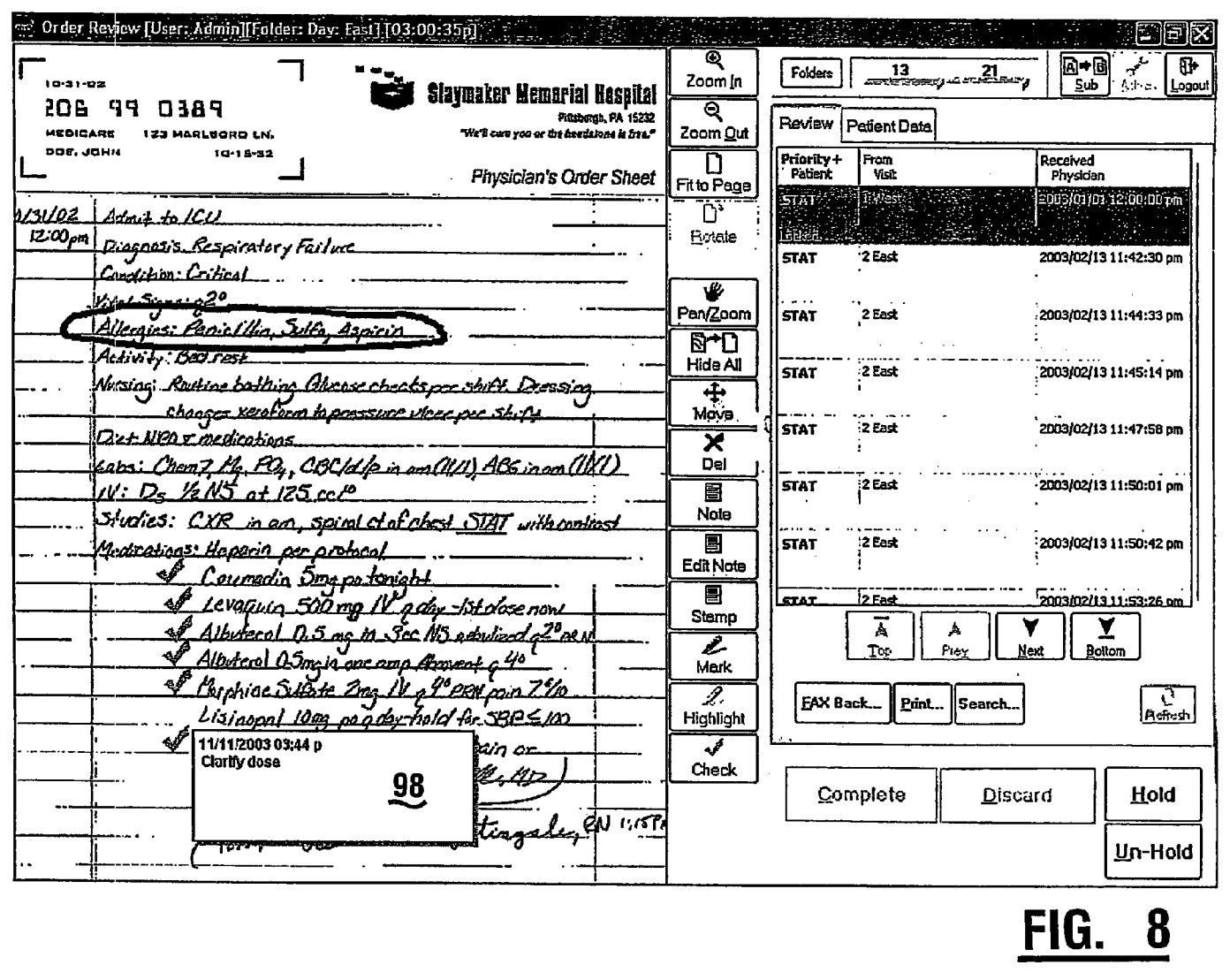

FIG. 8 shows an example of a physician order image that has been marked with checkmarks and a marking tool. As can be seen, the marking tool was used to circle a particular item in the imaged physician order. These virtual markings in the exemplary embodiment are represented by data in a database associated with the order image. These virtual markings can be stored in accordance with the programming of the computer to become a permanent integrated part of the physician order image data or to be separable therefrom. The approach taken will depend on system configuration. An annotated physician medical order including a comment can be stored in a single file. Alternatively, annotated physician medical order including a comment can be stored in plural associated files. For example, a comment can be separately stored in a file that is in correlated relationship with a file containing the originally received physician medical order. A pharmacist at a work station has the option of displaying an image of the annotated physician medical order or only the image of the originally received physician medical order. Each dated annotation can be stored as a separate file that can be layered over preceding annotation layers during display of the annotated order. A pharmacist is able to backtrack to view changes in an annotation history of a physician medical order. Of course these approaches are exemplary, and other storage methods enabling the viewing of annotation history can be used.

Figure 9:
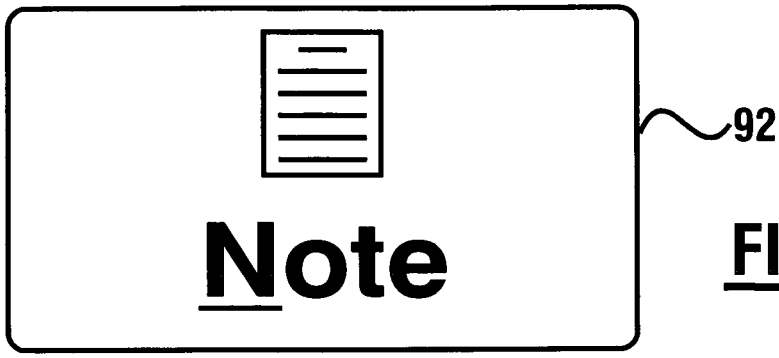
FIG. 9 is an icon associated with a note tool provided by the exemplary pharmacist work station.

A further feature of the exemplary embodiment is a note tool. This is represented in FIG. 3 and the note tool icon 92 which is shown in more detail in FIG. 9. The note tool icon 92 enables a user to enter or place a note in the image at a desired location. Selecting the note tool icon 92 and then touching or clicking (e.g., with a mouse or key) on a screen location places (or affixes) the note on the image at that specific image location. A note comprises a note area. The work station enables a user to define the size and/or shape of the default note area. Thus, a default note having a predefined area can be attached to an image at a particular image location.

In the exemplary embodiment the note is automatically stamped so as to include the date and time of the note. Furthermore, pressing a right arrow key on the keyboard 50 enables the pharmacist to include text within the note area. The text added to the note may be text typed by the pharmacist, or text already predefined and retrieved from a data store, or text written using a previously discussed marking tool (associated with mark tool icon 90). After text entry into the note is finished, pressing the enter key on the keyboard completes the note.

Figure 12:
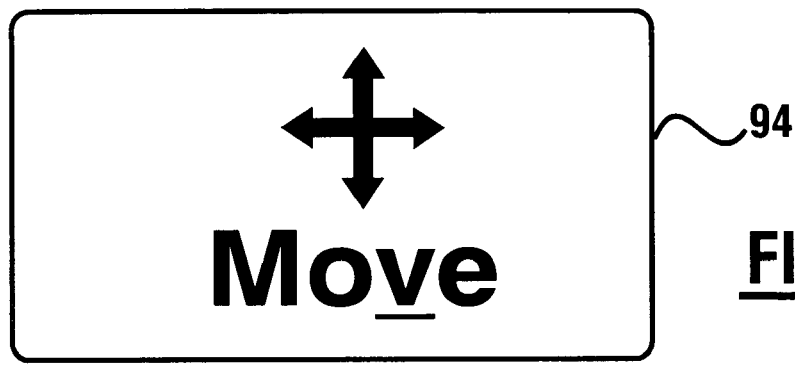
FIG. 12 is an icon associated with a move tool.

Further, a move icon 94 which is shown in FIG. 3 and which is also shown in greater detail in FIG. 12, can be selected to enable a user to move an inserted note so as to reposition the note in the image once it has been applied. This is done by selecting the move icon 94 and then touching the touch screen or moving the mouse to a desired screen location and clicking. This will cause the note to be imposed at that location in the order image.

Figure 10:
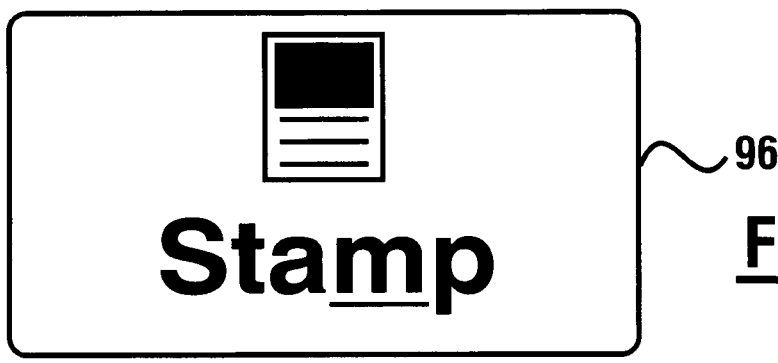
FIG. 10 is an icon associated with a stamp tool.
Figure 11:
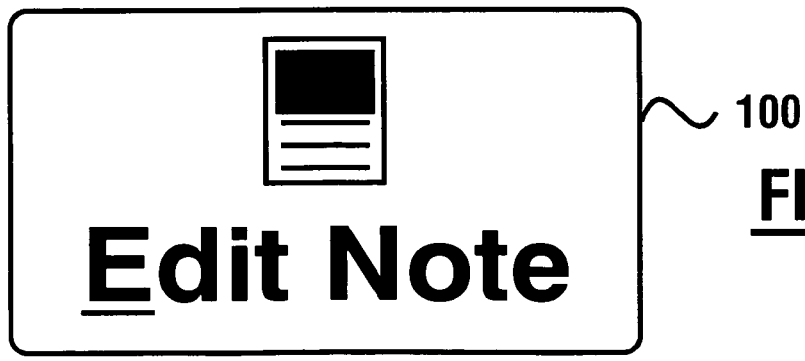
FIG. 11 is an icon associated with an edit tool.

The exemplary embodiment also includes a stamp icon 96 represented in FIG. 3 and shown in more detail in FIG. 10. The exemplary stamp tool is a special version of the note tool. The stamp tool enables use of a user-defined library of predefined messages or comments that are automatically placed in a note without any required typing. That is, a note already containing predefined text can be accessed for insertion. Predefined notes can be selected so that a user does not have to add (e.g., type) the text into a note area. Selecting stamp icon 96 causes a window to appear which includes a drop down list of predefined notes. A particular note is selected by providing an input using the mouse or touchscreen. Thereafter, touching or clicking on the order image places the note with its predefined text in the indicated location on the image. In addition, the move icon 94 shown in FIG. 12 can be selected for purposes of moving a predefined stamp. FIG. 8 shows an exemplary form of a predefined note or stamp 98 attached to or placed on an image of a physician medical order. In exemplary embodiments, notes and stamps may be placed in overlying relation in the image, and later separated as desired by selecting the move icon 94 and function.

A further function provided through the exemplary order interface screen shown in FIG. 3 is an edit note function. The edit note icon 100 may be selected by a user to enable the pharmacist to modify the text included within a note or stamp. Thus, a pharmacist may supplement text already included in a pharmacist-created note or in a predefined stamp to tailor it to a particular order image. Alternatively, a note previously presented can be modified based on information which a pharmacist receives or discovers which may necessitate a change. The edit note feature also enables a user to modify the size or dimensions of a note area.

Figure 13:
FIG. 13 is an icon associated with the fax back tool.

Another function provided in the exemplary embodiment of the pharmacist work station is the ability to fax back a message to an originating fax machine at a work station or to another location. This function is achieved by selecting the fax back icon 102 shown in FIG. 3 and in more detail in FIG. 13. In the exemplary embodiment, clicking on the fax back icon 102 causes a window to be displayed which includes data representing a list of nursing stations and other locations from which faxed physician orders have been received. The originating fax station for the particular order being handled in the display is automatically highlighted in the list. A fax transmission button is also presented in the window, and clicking on the window button causes an annotated fax corresponding to the modified or annotated order image to be automatically sent back to the originating fax station. The annotated fax may include the entire original physician medical order (with the annotated markings thereon) or only a portion of the original physician medical order. For example, only the physician medical order page having the annotated marking thereon may be faxed back to the originating nursing station.

Alternatively, the pharmacist is enabled to select a different station to receive the annotated fax by clicking on or touching an alternative station in the list so as to select it. This enables the pharmacist to direct the return fax to another appropriate station such as the requesting physician's office. This feature enables the pharmacist to direct an annotated fax image back to the particular location or person originating it so as to obtain clarification or other information that may be necessary to complete the physician order. In exemplary embodiments, if a pharmacist (or other person authorized to operate a work station) desires, multiple faxes corresponding to the same annotated fax image may be sent to different locations.

A return fax may be received at a nursing station as a printed paper fax via a paper receiving fax machine at the nursing station. A nurse or physician can respond to a pharmacist's question in a received annotated physician medical order paper fax by marking directly on the paper and then transmitting it back to the pharmacy.

It should be understood that a return fax may be transmitted from the pharmacy as an electronic image corresponding to an annotated (or modified) physician medical order. For example, a modified physician medical order can be sent from the pharmacy to the originating nursing station. The nursing station can have a computer and display device capable of receiving and displaying the electronic image. The nursing station computer can have fax receiving and fax sending software. The pharmacy-added markings on the annotated physician medical order can be viewed at a nursing station display screen. A nurse or physician can respond to a pharmacist's question in a received modified or annotated physician medical order by transmitting another fax to the pharmacy. The response (second) fax can be sent electronically from the nursing station to the pharmacy via the nursing station computer using fax sending software. Alternatively, a response message can be first be printed out on paper and then faxed via a paper receiving fax machine to the pharmacy. Similarly, the original fax from the nursing station to the pharmacy can be both sent and received as a paper fax. In an exemplary embodiment the nurse stations (and the pharmacy) are able to transmit and receive both electronic faxes and paper faxes. Also, the electronic faxes may be transmitted and received wirelessly.

As also represented in FIG. 3, the exemplary pharmacist work station includes other function buttons 62 that can be selected responsive to inputs. These function buttons include a complete button 104 which is normally selected by a pharmacist when they have completed placing entry of the physician order data into the pharmacy order system. In an exemplary embodiment, upon completion of an order entry, an annotated physician order image is saved and the next image in the priority ordering is presented.

A discard button 106 is also provided. The discard button 106 can be selected when a pharmacist is required to discard the image. This may be done for numerous reasons. For example, in response to an inquiry from the pharmacist, the physician responsible for the order may request that the order be canceled. Furthermore, the patient to whom the physical medical order was directed may have expired and will not be needing the medication.

A hold button 108 is also provided. The hold function is generally selected when more information on an order is needed. As previously discussed, orders at an upper or top area of the queue have a higher priority than orders at a lower or bottom area of the queue. In the exemplary embodiment, placing an order on hold temporarily moves it to a position at the bottom of the order queue until a time out value is reached. Thereafter it is moved to the top of the order queue to determine if the desired additional information has been received. This feature helps to minimize the risk that a medication order will be lost. The time period assigned to the time out value can be defined and/or adjusted by a work station user. Orders that have been placed on hold can be released manually by selecting an un-hold icon 111. Selecting the un-hold icon 111 will release the order earlier than the timing function.

In the exemplary embodiment, a selection of the complete 104, hold 108, or discard 106 buttons by the pharmacist causes the image to no longer be (currently) displayed at the pharmacist work station, and the next image in the queue that is available for processing is presented in the display. Of course, the data corresponding to the previous image is stored in the database associated with the interchange fax station for archive, later review, and/or further processing. Of course these approaches are exemplary and in other embodiments other approaches may be used.

Figure 14:
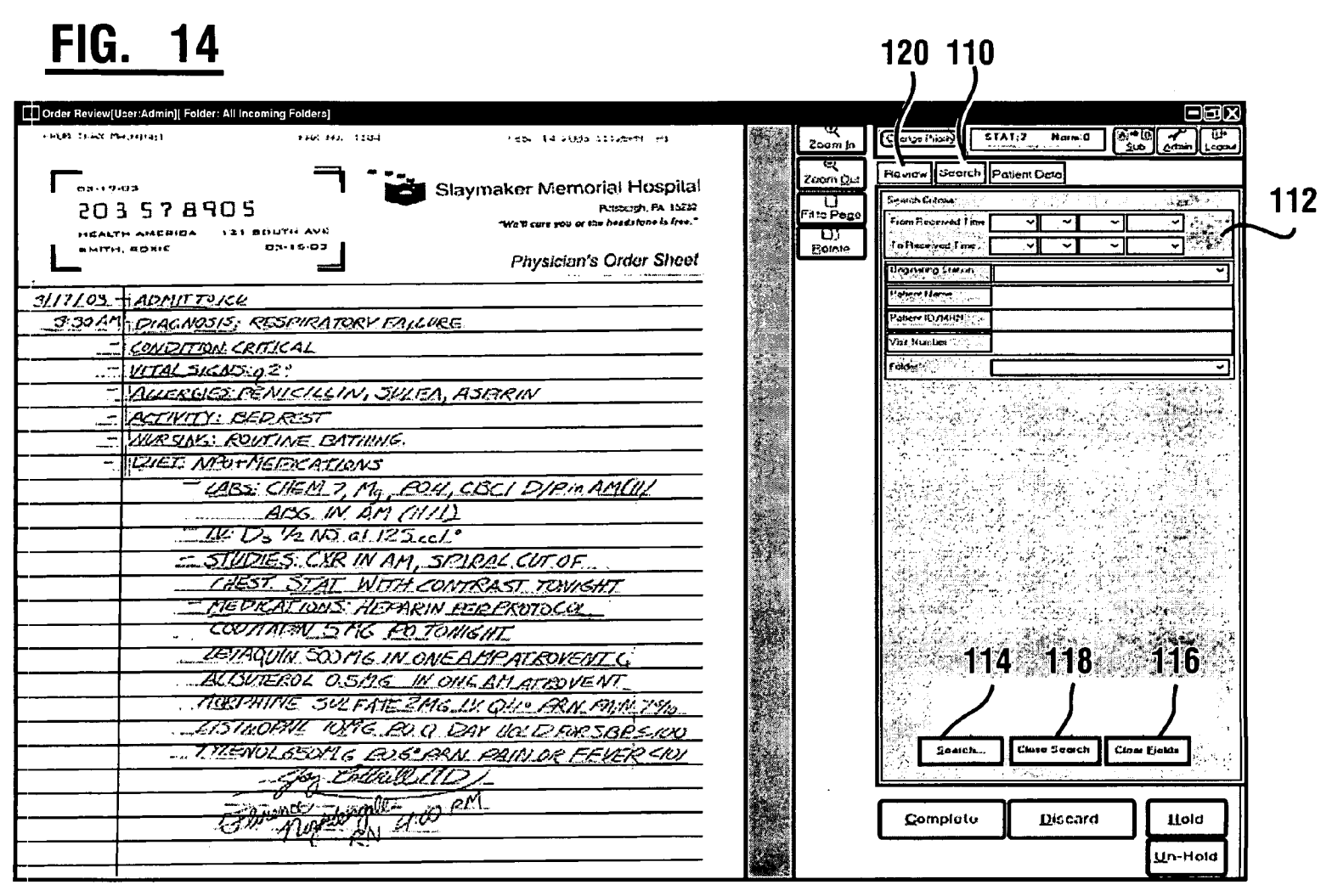

As further represented in the order review interface screen in FIG. 3, a searching function is provided through the programs executable in the exemplary pharmacist work station. Selecting the search button 110 causes a search folder 112 to be displayed on the right side of the order review interface screen, as shown in FIG. 14. The format of the physician order review interface screen shown in FIG. 14 includes the displaying of a search folder window. Selecting the search function provides a matrix which a user can populate with search criteria. This matrix is shown in greater detail in FIG. 15. By populating the data in this matrix and selecting the lower search icon 114, the user may search for orders that meet the user's selected criteria. The orders that are uncovered in the search are output to the left side of the exemplary output screen. In the exemplary embodiment, a user may conduct multiple searches, and change search data by inputting different criteria and clearing prior criteria. This is done by selecting the clear fields icon 116. The displayed search folder can be closed by actuating a close icon 118 or by selecting the review icon 120, which places the screen back in the display format shown in FIG. 3.

Figure 15:
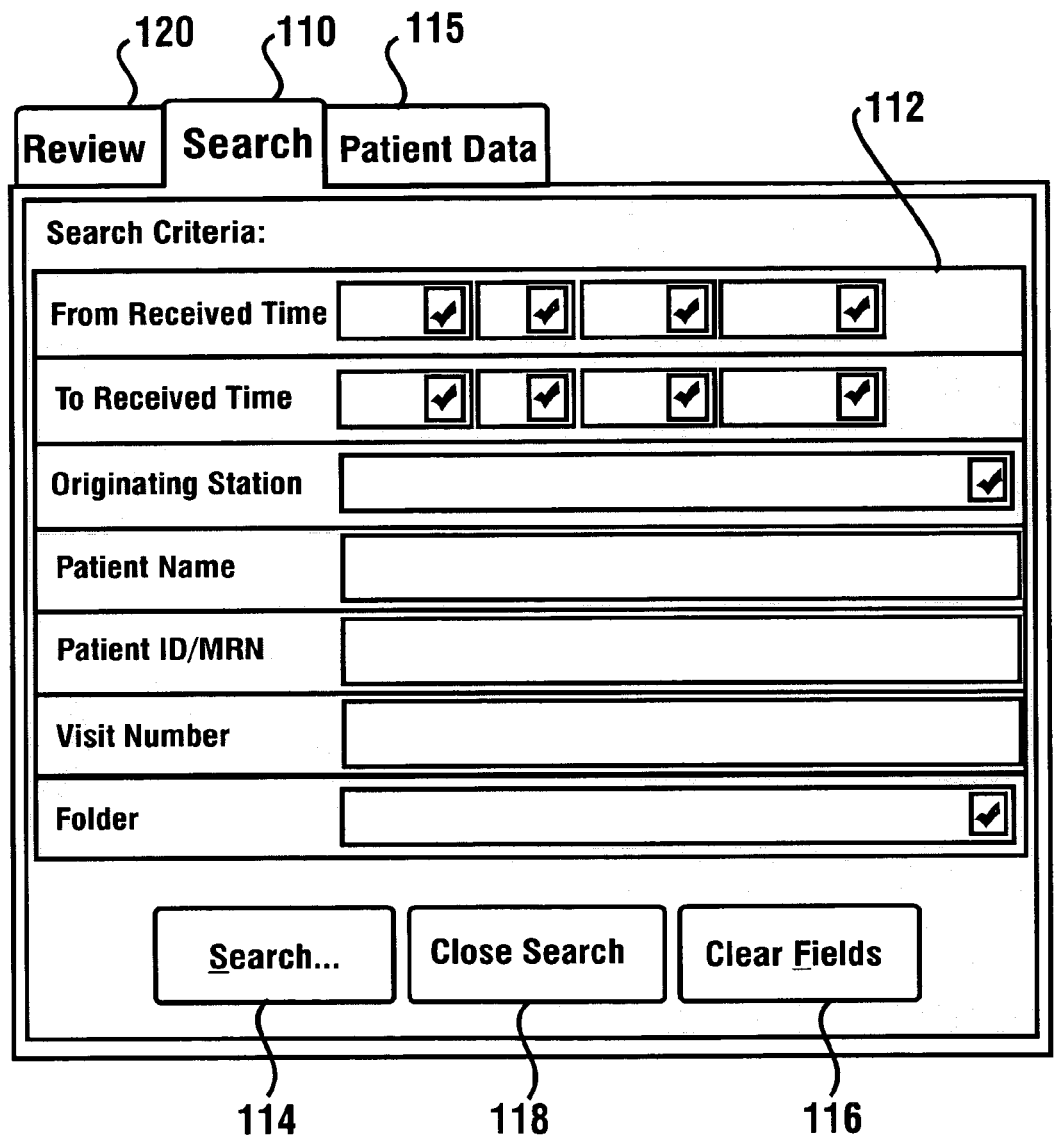
FIG. 15 is an enlarged view of a portion of an output screen which is populated by a pharmacist in order to search for a faxed order.

Another screen format available for display can be selected by using the patient data button 115 shown in FIG. 3, with an enlarged view shown in FIG. 15. Upon using this screen icon, data corresponding to a particular patient is displayed in a patient data window. The particular patient can be the patient corresponding to the currently displayed physician order. Also, the particular patient can be the patient retrieved in a search result. Data from the pharmacy order entry system regarding the patient's name, ID, date of birth, ward, room, and other information can be displayed for review at the pharmacist work station. As previously discussed, besides a patient data window, the pharmacist work station enables the screen display of several other windows, including a queue window and a search folder window.

It should be understood the positions of the displayed buttons described herein are exemplary. In other exemplary embodiments the buttons may be relocated in a display. For example, FIG. 8 shows a search button located adjacent to the print button. It should also be understood that in other exemplary arrangements additional or fewer buttons may be used. For example, the order review interface screen of FIG. 3 shows an additional close search button. The screen of FIG. 8 shows a refresh button. The refresh button can be used to redisplay the current image. When work stations are connected to the Internet, the refresh button can also be used to reload the current web page. In additional exemplary embodiments the workstation operator has the option of selecting which operator buttons are to be displayed.

In an exemplary embodiment, pharmacists are also enabled to achieve therapeutic substitution for medications to be provided to patients. A physician issuing the medication order will write the order listing the medications they want the patient to receive. Generally the pharmacist takes these orders, reviews them and if there are no issues, inputs the data to the pharmacy order system to create a medication order for the patient. These medication orders result in the medication being provided to the patient through the operation of the hospitals' medication delivery systems.

However, in some cases the hospital by policy allows for medications to be substituted. This process may be referred to as therapeutic substitution which may be a medication substitution or changing an aspect of the prescription as originally written before entry into the pharmacy system. An example may be substituting one brand name medication for another or substituting a generic. Alternatively a substitution may include changing the dose, route or frequency of the particular medication. In some exemplary embodiments even though a pharmacist may be able to make the therapeutic substitution according to preapproved substitution policies, a new physician order must be created and signed by the pharmacist to document the substitution. Alternatively the identification system used to identify the pharmacist who operates the pharmacist terminal may be used to automatically input into the record the pharmacist's name.

In the exemplary embodiment, if the pharmacist inputs the substitute order and the physician does not agree, the physician will create a new medication order to discontinue the substitution and select a new medication.

Figure 16:
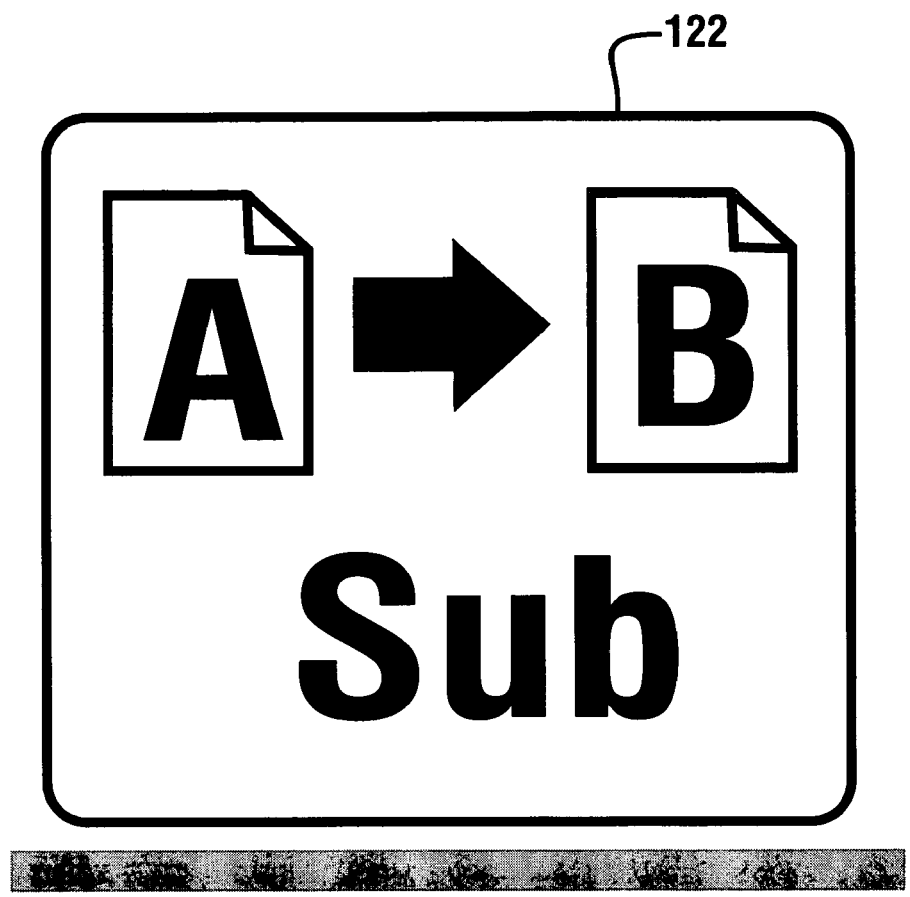
FIG. 16 is an icon associated with a substitution function provided the pharmacist workstation.

In the exemplary embodiment a pharmacist is enabled to accomplish a therapeutic substitution order by selecting the substitution order icon 122 shown in FIG. 3 and in additional detail in FIG. 16. Selecting the substitution order icon causes the physician order form 124 shown in FIG. 17 to be presented. In this form the pharmacist is enabled to select the physician ordered medication from a drop down list 126 indicated DC. The pharmacist is also enabled to select the medication, dose, route and frequency to be substituted from a drop down list 128 selectable in the "give" field. In the exemplary embodiment a predefined note associated with the medication that is being substituted is automatically placed in a note area 130 in the form. Additional information may be added to the note by the pharmacist clicking into the note and typing. Further as represented in FIG. 17 the pharmacist may sign the order in a signature area 132 with virtual electronic ink using the mark tool function. The originating nursing station from which the original order was presented is selected by the pharmacist work station by default to receive the completed physician order form. By clicking on or activating (e.g., via a mouse or keyboard or touch or voice command) the displayed send button 134 the pharmacist is enabled to send a fax of the therapeutic substitution form to the originating station. Further by clicking on the complete button 136 the substitution order is stored to the database. Of course these approaches are exemplary, in other embodiments other approaches may be used.

In an exemplary embodiment additional functions may be provided. For example, as shown in FIG. 3 a hide icon 138 is provided. The hide icon may be selected to review the order image without overlying markings. Selecting the icon again causes the markings to be restored.

A further exemplary function is the delete function which is selected using a delete icon 140. The delete icon may be selected, and then touching or clicking on a previously applied pharmacist marking, will cause the marking to be deleted. Such functions may be useful for correcting mistakes. It may also be useful for eliminating notes that particular information is needed once the information is received. In some exemplary embodiments the computer may be operative to store markings that were made and then deleted for purposes of providing a complete record of order processing. Of course, these approaches are exemplary.

The exemplary user interface screen also includes arrow icons 142 that can be used to scroll through the physician medical orders waiting in the queue 64. For example, arrows representative of top of queue, previous page, next page, and bottom of queue can be used, as shown in FIG. 3. A change priority icon 144 is also provided. The change priority icon can be used to change the status of a particular selected order from the normal category to the stat category; and vice versa.

Of course these functions and interfaces are exemplary and in other embodiments other or different functions may be provided.

Further, in the exemplary embodiment, a plurality of hot keys are provided to facilitate the rapid operation of the pharmacist work station by a pharmacist. These hot keys are basically a combination of keyboard inputs that enable the pharmacist to select the various functions without having to utilize the touch screen or mouse interface. The exemplary embodiment enables a pharmacist to become familiar with these hot key combinations so as to facilitate selecting desired functions without the normal selection activities. In some embodiments these hot keys may be predefined for the system. Alternatively, embodiments may be devised so that a pharmacist can establish their own hot key approaches to meet their particular preferences. Of course these approaches are exemplary of many approaches that may be used in embodiments of the invention.

Exemplary embodiments of the system may include a capability for an administrator to set certain parameters associated with the operation of the interchange fax station and pharmacist work stations. These may include, for example, setting work station settings, setting up user accounts, establishing hardware configurations, setting up folder configurations, providing the information for therapeutic substitutions, setting up notes and stamp configurations and predefining stamp language. Of course these administrative functions are exemplary and in other embodiments other approaches may be used. In the exemplary embodiment, administrator functions are accessed by actuating an administrator icon 146. Selecting this icon enables the user access to those administrative functions they have been authorized to access based on the setup of the work station.

Figure 18:
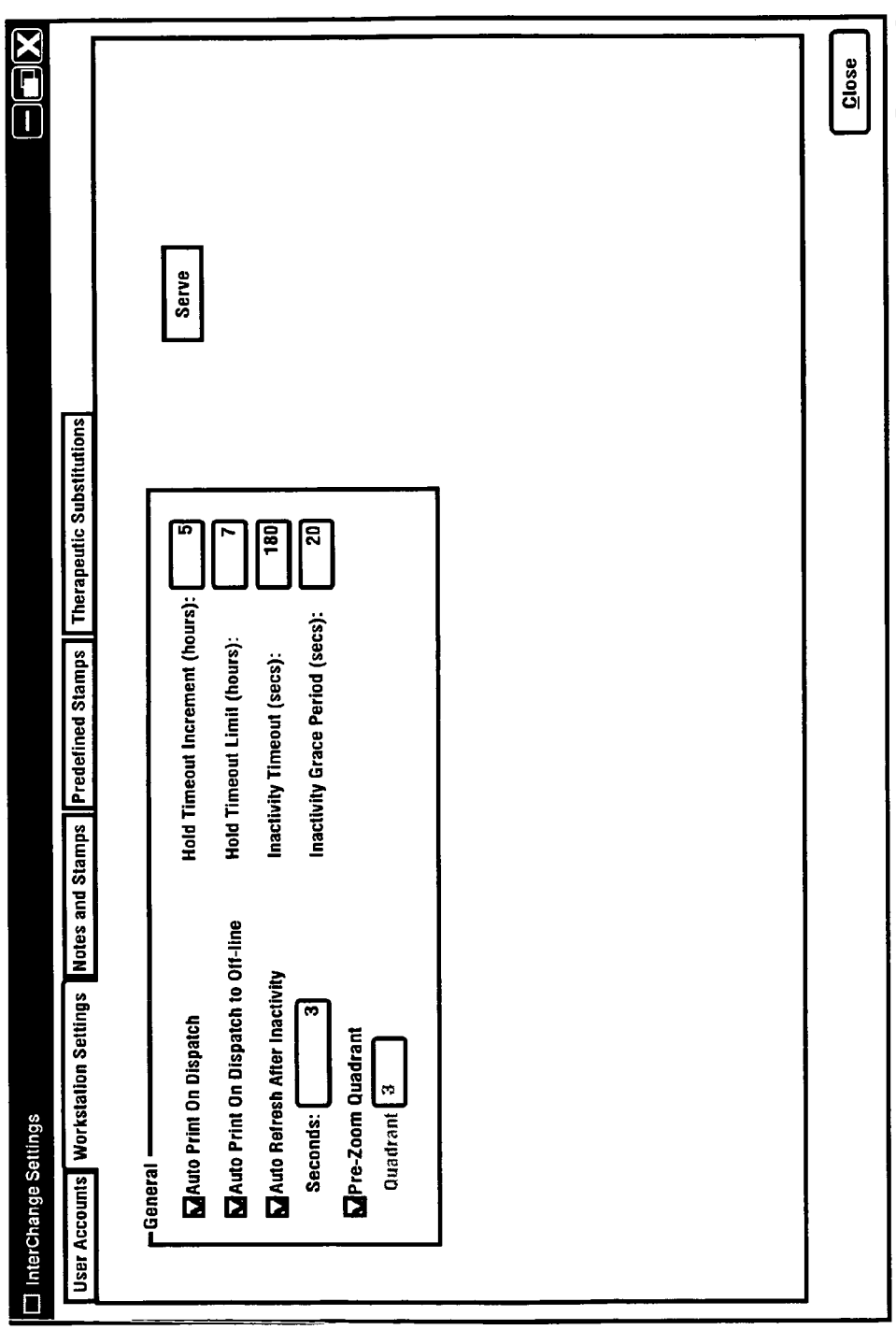
FIG. 18 is an exemplary screen output by a pharmacist workstation to access administration functions.

FIG. 18 shows an exemplary output screen from the pharmacist work station which is used in an exemplary embodiment to set work station settings. One option which is selectable from this screen is an autoprint on dispatch feature. When checked responsive to a user input the autoprint on dispatch feature executes programmed logic in the pharmacist work station to cause every image and/or annotation to be printed on a default printer.

Another option in the exemplary embodiment is an autoprint on dispatch to offline feature. This feature when selected sends every image dispatched to the offline folder and its annotations to the default printer. The offline folder is a special feature that allows the pharmacist to fulfill order requests while the pharmacy order system may be unavailable. This may occur due to malfunctions or other problems with the pharmacy order system.

Another feature in the exemplary embodiment is an auto-refresh feature. When checked responsive to a user input it refreshes the pharmacist work station at a rate that is specified through the input number of seconds indicated on the work station settings screen.

Another option configurable in the exemplary embodiment is a pre-zoom quadrant. When checked responsive to a user input, the electronic representation of a fax physician order will be first presented to the pharmacist zoomed-in on the specified quadrant. As previously discussed, this may be useful for reading the patient's name and user ID or medical record number (MRN) for entry into the pharmacy order system. In the exemplary embodiment the user is enabled to specify or select through an input provided through a drop down menu, the quadrant which is to be initially zoomed. Quadrant 1 is the upper left area of the physician order image. Quadrant 2 is upper right. Quadrant 3 is lower left and Quadrant 4 is lower right. A quadrant can be enlarged to encompass the entire display screen area. The selected quadrant can be the default quadrant until changed. As previously discussed, the pre-zoom quadrant feature can be set by the user so that the first image displayed on the display screen is the default-selected zoomed quadrant. Thus, an enlargement of a preselected image location or defined image area can be the initial or default screen automatically displayed when the physician order image is first selected for display. It should be understood that in other embodiments other areas of a screen may be specified for purposes of providing automatic zooming, abstraction, or maximization depending on the programming of the pharmacist work station. For example, the borders of a quadrant can be user-defined by using drawing tools to electronically describe or outline the desired quadrant area on the display screen. Thus, a new quadrant, such as one overlapping areas of quadrant 1 and quadrant 2, can be created, saved, and used again.

Another option in the exemplary embodiment of the work station settings shown in FIG. 18 is the hold timeout increment. The hold timeout increment specifies in hours the amount of time to keep a physician order on hold each time that the hold button is selected. The hold timeout increment is the standard time that will be provided when a hold is first specified. As previously discussed, a time period assigned to the time out value can be selected by a work station user.

Another option of the exemplary embodiment is a hold timeout limit, which corresponds to the maximum number of hours that the system will allow an order to be placed on hold. Thus, for example, if a pharmacist has to place an order on hold multiple times, once the hold timeout limit is reached, the order will rise to the top of the queue and cannot be placed on hold again. A time period assigned to the hold timeout limit can be selected or defined by a work station user. A hold timeout limit can be adjusted to encompass or correspond to cumulative time out values. For example, a time out value and a hold timeout limit can each be set relative to each other to ensure that a fixed number (e.g., three) of holds can be placed on an order. Once the set number of holds on an order has expired, no more hold for that order is permitted.

It should be understood that the maximum time that an order can be placed on hold may expire while the current hold timeout increment (timeout value) has not yet expired. When the hold timeout limit is set as having priority over any hold timeout increment, then the order will be placed near the top of the queue. In other embodiments, the hold timeout increment and hold timeout limit can be set relative to each other so that a current hold timeout increment will continue until its expiration regardless of the hold timeout limit expiration. However, because of the hold timeout limit expiration, no more holds on that order are allowed to begin.

It should also be understood that a non-urgent order released from hold may be positioned adjacent to or near the top of the queue, instead of at the very top of the queue. The queue can be setup so that urgent orders always stay at a (reserved) top portion of the queue. Thus, a non-urgent order released from hold can be moved from the bottom area of the queue to the top area of the queue directly below any urgent orders. In other embodiments, an order identified or labeled as urgent cannot be placed on hold.

In an exemplary embodiment, an out of hold time notification can be made available to the operator of the work station when the maximum time limit has been reached. For example, the order represented in the display queue may be flagged with a particular mark or different color indicative of being out of hold time. Likewise, an out of hold time notification or warning can be immediately displayed on the display screen (or an audible signal activated) when the hold button is selected and there is no more hold time remaining.

A further option is the inactivity timeout. The inactivity timeout specifies the amount of time in seconds that a user's session remains active without any keyboard or mouse activity. When this time interval expires, the pharmacist work station will wait the additional number of seconds specified in the indicated inactivity grace period field. After the grace period expires the user is automatically logged off the system. This feature is useful in an exemplary embodiment to assure that pharmacist work stations are not left unattended for extended periods of time in which unauthorized persons can gain access to the system and the associated confidential information contained therein. Of course these pharmacist work station configurable settings are exemplary and in other embodiments other configurations may be used.

Another administration function which can be set for one or more pharmacist work stations by an administrator is user account information. This can be accessed by an authorized administrator by selecting the user accounts administrator folder tab from the administrator menu. Such a selection is represented by the screen output shown in FIG. 19. From the user accounts window an administrator is enabled to add, modify or delete user accounts and assign access rights for particular pharmacist or other users. In the exemplary embodiment the pharmacist work station is programmed so that the administrator can also disable a user account temporarily such as when a user is on vacation.

Figure 19:
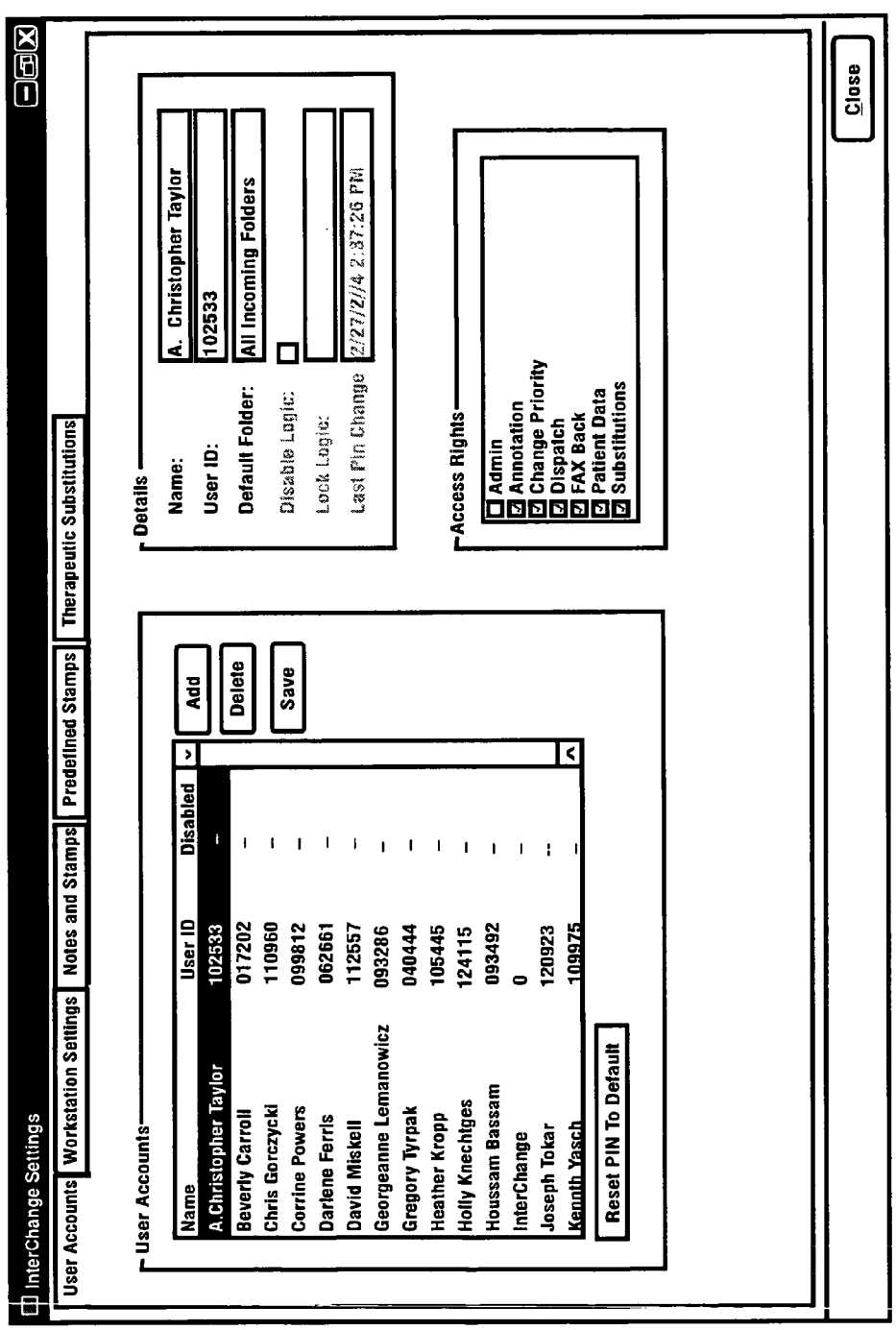
FIG. 19 is a screen output associated with setting up user accounts in an exemplary system.

As represented in FIG. 19 an administrator can set numerous parameters for a given authorized user. These features and functions include the authorized user's name and user ID. As previously discussed this user ID is used to sign on the pharmacist work station may be input manually or via a card or other article. Also in the exemplary embodiment, when first established user accounts have a default PIN which the user is provided and which can be used for the first user login. However the user is prompted on that first login to set their own unique PIN which is unknown to anyone but them. Further in accordance with parameters established through the programming of the system the user may be required to change their PIN periodically.

Other options which can be set through the user account configuration window shown in FIG. 19 include the setting of a default folder. This is a category or a "folder" that the user will review after logging in. The default folder selection is generally configured as a drop down list of various options. Most often this is set to all incoming faxes, but it may be set in other situations to other categories of items such as physician orders coming from particular nursing stations or items that have been placed on hold.

Other options that can be set by an administrator through the user account window include the disable login function. Disable login when checked, disables the user account. Outputs are also provided through the exemplary user account window indicating the last login for the user as well as the last time that the particular user has changed their PIN. User details are selected by highlighting a name in the left-hand portion of the window. Further as indicated in FIG. 19 there is also a selection that enables the administrator to reset the PIN of a particular user to a default value. This may be done, for example, if a user is concerned that their PIN data has been compromised and they wish to set a new PIN the user may do so on the next login after the existing PIN has been cleared.

As represented in FIG. 19 users may be selectively provided with certain access rights. The particular access rights provided to a particular user are indicated for the user whose name is highlighted in the left-hand portion of FIG. 19. Rights can be provided to a user by inputs by an administrator that result in checkmarks in boxes. These rights may include administrative rights that allow the particular user to have access to all the administrative functions. This is generally provided only to persons in a supervisory position. Other rights include annotation rights which enable a user to make and save annotations on electronic representations of orders. A change priority selection enables a user to raise a priority of a particular medication order from normal to stat, as well as to lower a priority from stat to normal.

The dispatch access right enables the designated user to dispatch an image. The fax back authority allows a user to send an image either back to the originating fax machine, to a predefined department fax machine or to other fax machines. Selecting the patient data access right allows a user to manually add data to patient data fields. Selection of the substitution right enables the authorized user to make a therapeutic substitution. Of course these rights are exemplary and in other embodiments other or different access rights may be provided.

Figure 20:
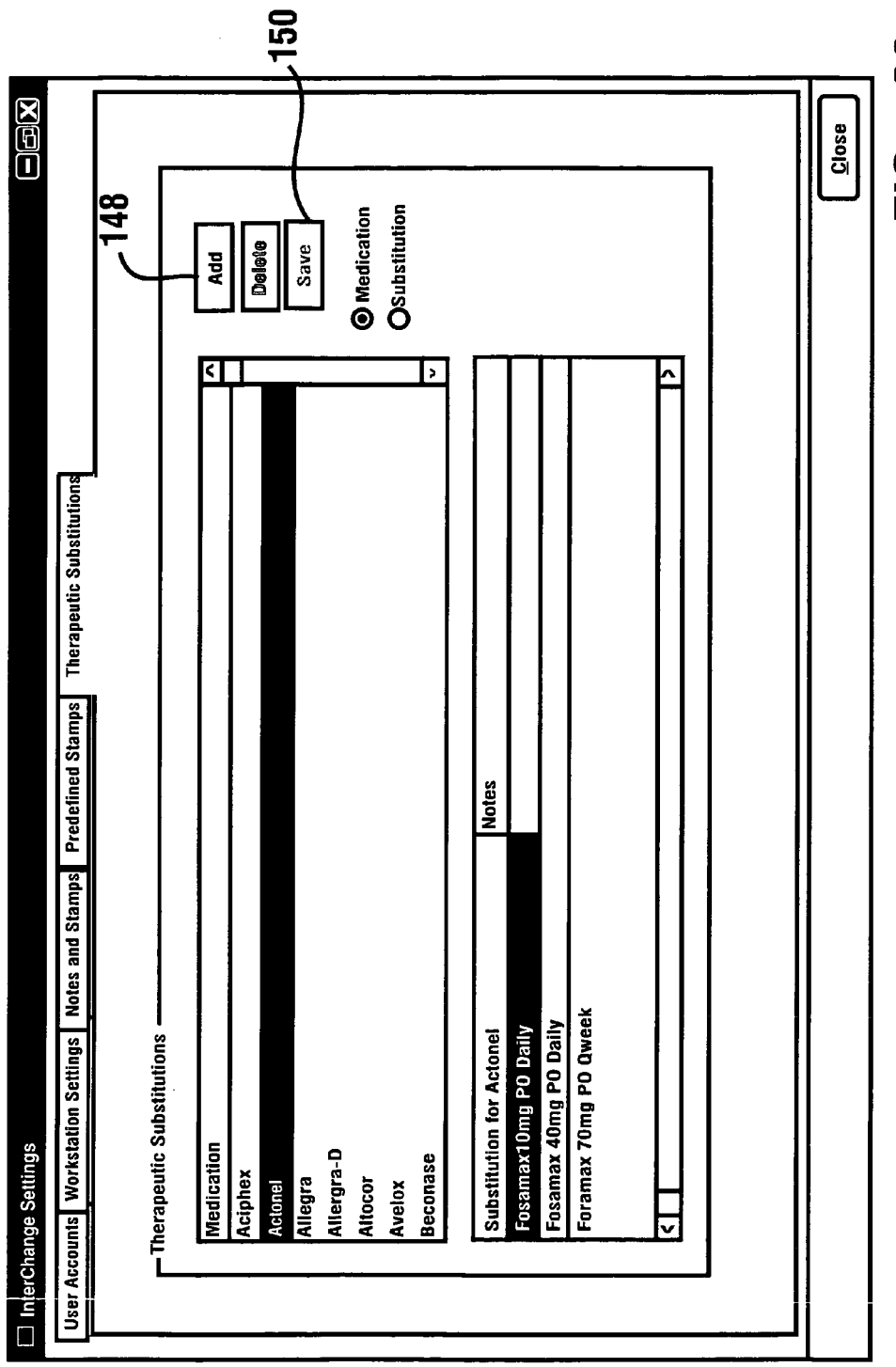
FIG. 20 is an exemplary output screen associated with setting up therapeutic substitutions that may be allowed in an exemplary system.

Certain of the access rights have associated menus and other functionality that is established through the programming of the pharmacist work station or interchange fax station. One of these as indicated by the tabs in the administrative menu is the therapeutic substitution capability. In the exemplary embodiment, selection of the therapeutic substitution folder by an administrator causes the output of the therapeutic substitution screen shown in FIG. 20. There are two portions or windows associated with the screen. The upper portion contains the medication for which a substitution can be made. When a particular medication is highlighted in the upper window, the lower window shows the nature of the approved substitutions. In exemplary embodiments a medication may have more than one approved therapeutic substitution. These substitutions may be, for example, another medication, a medication dose, administration frequency, administration route or other substitution criteria. As previously discussed, approved therapeutic substitutions may be set in accordance with hospital policy or some other medical policy. For example, a hospital pharmacy can have medical substitutions (e.g., medicines, devices) set in accordance with authorized substitution tables and rules located in a data store that is accessible by the pharmacist work station.

In the exemplary embodiment an administrator may add a new medication to the therapeutic substitution by selecting the add button 148. After selecting the add button the desired medication name is input and selecting the save button 150 saves the particular medication. The associated substitution for this medication is added by clicking into the lower window shown in FIG. 20 and selecting "yes" when prompted to add a new substitution for the medication selected in the upper window. This can alternatively be accomplished by selecting the substitution radio button on the right-hand side of the screen.

An authorized administrator may edit medications and their substitutions by placing the mouse pointer into the text to be changed, modifying the existing text and selecting the save button 150. In the exemplary embodiment, if an administrator makes a change and attempts to change another medication or substitution or to close the window without saving, the pharmacist work station is operative to cause a prompt to appear asking the user if they want to save the changes. Selecting a "yes" button that appears saves the changes. Pressing a "no" button discards the changes. Of course this interface approach is exemplary and in other embodiments other approaches may be used.

Figure 21:
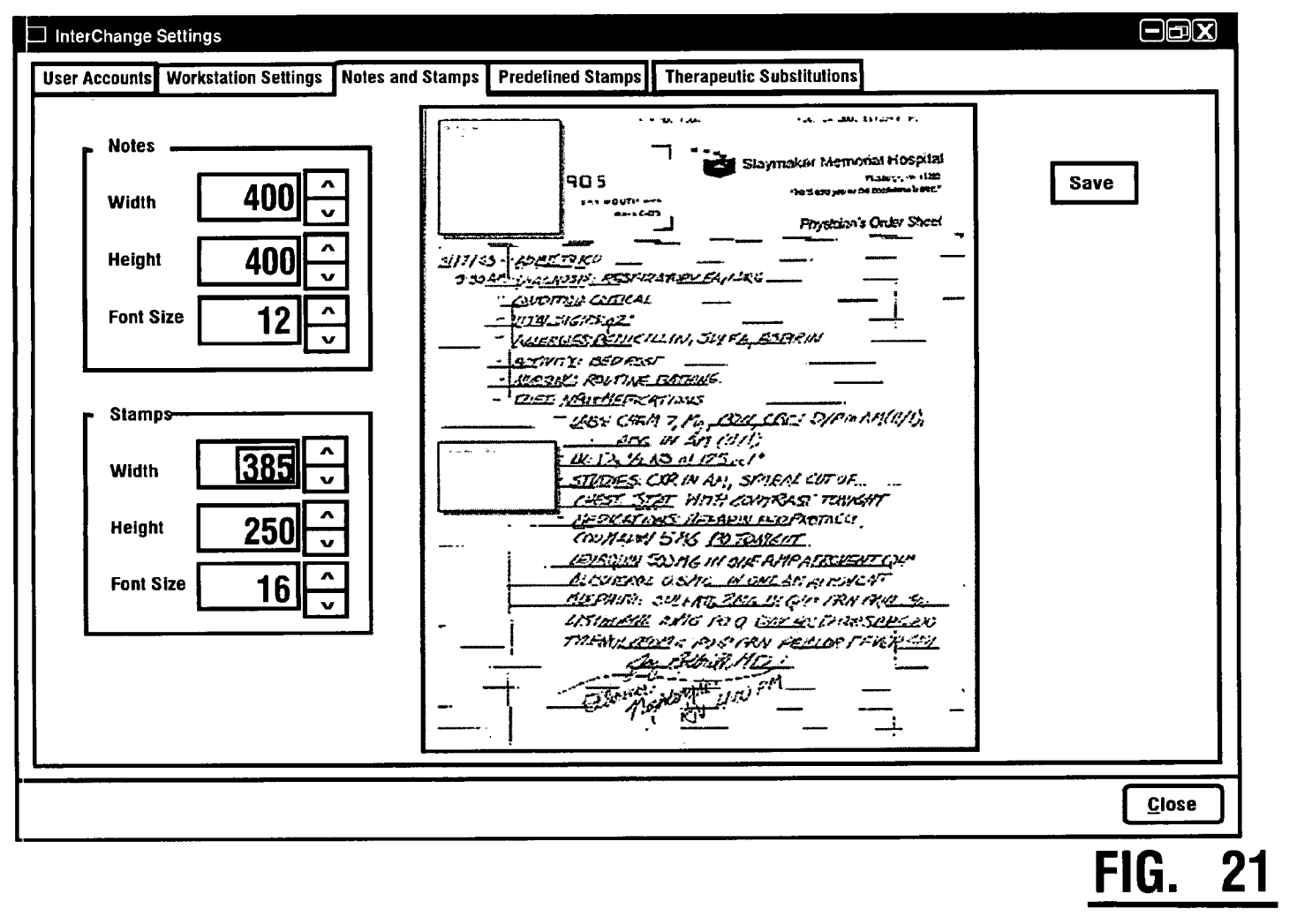

FIG. 21 shows the setup that an administrator may use associated with the note and stamps configuration folder that is accessible by an administrator. The notes and stamp configuration function allow a default width and height, as well as text font size to be used in conjunction with applying notes and stamps to electronic fax images. Electronic representations of note and stamp boxes are displayed over a sample fax image to help the user visualize the size of these boxes and their fonts. This is represented in FIG. 21.

An administrator may input values into the width, height or font size fields or up and down arrows may be selected by a user to make desired size adjustments to the default size for notes and stamps. In the exemplary embodiment the ability of the administrator to set the default size of the notes and stamps facilitates placing such markings in a suitable size in the electronic images so as to facilitate the readability of both the original fax image as well as the markings applied thereto by the pharmacist.

Another folder that may be selected by an administrator from the administrative menu are the predefined stamp settings. Selecting this folder results in the administrator being presented with the predefined stamp output screen shown in FIG. 22. As previously discussed stamps are made to include predefined text which is frequently used by a pharmacist to indicate some aspect of the physician order. For example, stamps frequently used by a pharmacist may indicate a need for a particular type of clarification associated with the physician order. Some exemplary stamp text content is represented in FIG. 22.

Figure 22:
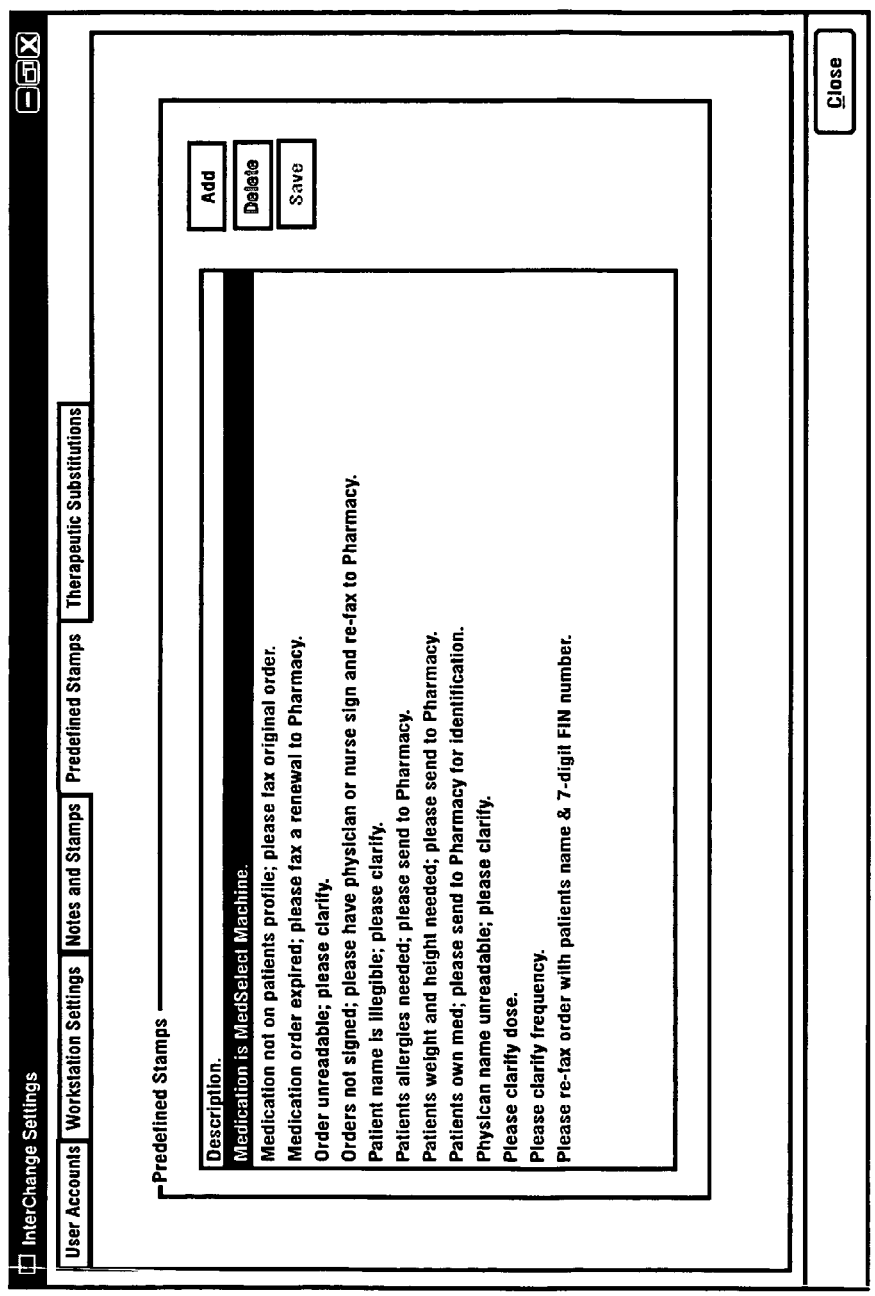
FIG. 22 is an exemplary screen for inputting predefined text to be included in stamps applied by pharmacists on physician order data.

In exemplary embodiments, stamps may be created for storage in a data store associated with the pharmacist work stations by selecting the "add" button shown in FIG. 22. The administrator then enters the desired text and selects the save button. In an exemplary embodiment, stamps can also be edited by placing the mouse pointer into the text to be changed and making the modifications. Once the modifications are made the user may select the save button. Provisions are also made for reminding a user who has inserted a changed stamp text to save the text as changed if they have not selected the "save" button before attempting to close the window. Of course these approaches are exemplary and in other embodiments other approaches may be used.

It should be understood that in some exemplary embodiments the pharmacist work station or other computer may be programmed so as to selectively provide the administrative functions to various persons. For example, in some embodiments the system may be configured so as to strictly limit access to administration functions to particular individuals. In other embodiments, systems may be configured to allow authorized users who do not have formal administrative access to nonetheless access certain aspects of the system such as to set note and stamp sizes or to create customized stamps related to the particular type of physician orders that they may be handling.

In operation of an exemplary embodiment of the system, a physician writes an order for one or more medications that a patient is to receive. This may include the completion of a form or other document which sets forth information about the patient, their condition, diagnosis, vital signs and other information that the pharmacist may be required to know. FIG. 3 shows an example of an order with some of the information that may be normally included on such a form. When the physician or his designee has completed the form, the physician will generally sign the form and provide it to a nurse. It should be understood that although in the exemplary embodiment the use of a paper form is discussed, in alternative embodiments physician orders may be electronically created and signed electronically such as with digital signatures, signature representations, facsimiles, or other suitable indicia of authenticity which shows that the physician responsible has approved the particular order.

In the exemplary embodiment, once a physician order has been completed and signed, a nurse will place the physician order in a fax machine located at the nursing station. The nurse has the option to send the fax either to the high priority phone number or extension number for receiving stat faxes, or to another number which is designated for normal priority orders. In exemplary embodiments the fax machine used will generally be preprogrammed with these numbers so as to facilitate the nurse sending the fax rapidly to the appropriate number.

It should be understood that in alternative embodiments other methods of capturing and dispatching image data may be used. These may include, for example, scanning the particular physician order document at the nurse's station so as to provide the document in a format other than a fax format. This may also include adding the electronic representation to a database that is accessible by the computers in the pharmacy rather than specifically dispatching the particular image to a particular phone number. Of course when physician orders are created electronically, other approaches consistent with the manner of inputting the physician order may be used.

In the exemplary embodiment, after the nurse has dispatched the fax to the pharmacy the electronic image represented by the fax is received by the computer which makes up the interchange fax station 28 in the pharmacy. The computers are operative to place the order in queue in accordance with the priority assigned to the order and the time of receipt.

Pharmacists working at pharmacist work stations are automatically presented with the next fax in the queue. This is done in accordance with the administrative settings set for the particular system. Generally however the system is configured so that the faxes having the highest priority are presented first. These would include the stat orders or normal orders that have been waiting the longest. Of course as previously discussed, orders that have been placed on hold will automatically be sent to the top of the queue through operation of the computer once the hold period has expired.

As previously discussed in an exemplary embodiment and in accordance with the administrative settings, the image of the medication order can be automatically zoomed to the defined quadrant so as to readily show to the pharmacist information such as the patient name and ID number. In response to reviewing this information the pharmacist will then use input devices to call up the corresponding data for the patient through the connected pharmacy order system. As previously discussed in the exemplary embodiment, this is done through the input devices such as the mouse and keyboard of the pharmacist work station. Further in an exemplary embodiment the outputs produced by the pharmacy order system will be generated an output through the second screen attached to the pharmacist work station.

The pharmacist will then review the physician order for medications and will take the appropriate action. This may include putting the information into the pharmacy order system. It may also include providing appropriate annotations on the electronic image of the order, faxing the annotated image back to the originating fax station or to another source, placing the order on hold, discarding the order or taking other appropriate action. Upon the pharmacist completing the order, placing the order on hold, or discarding the order, the image data including the annotation data is stored to the database in association with the interchange fax station. The pharmacist work station and interchange fax station then operate in accordance with their programming to present the next physician order to the pharmacist for handling.

It should be understood that in exemplary embodiments provision may be made for recovering and storing physician order data in its original form without modification as well as recovery of the order with annotations. This may enable users to selectively produce the original order or the annotated order as desired. In addition, in some embodiments, provision may be made for assuring that the original physician order and/or annotated physician order version are verifiable as not having been changed subsequent to entry of the order into the pharmacy system. This may include, for example, having the interchange fax station, pharmacist work station, or both applying appropriate digital watermarks, verification codes, authentication indicator, or other suitable means that helps to assure that the particular data stored is accurate and original. Of course these approaches are exemplary and in other embodiments other approaches may be used.

Systems operated in hospitals and other medical facilities may be used to facilitate the delivery and tracking of medication orders that are prepared by pharmacists and included in the pharmacy order system. Exemplary devices, systems and methods for such systems are shown in the following patents and applications which are owned by the assignee of the present invention and the disclosures of which are incorporated herein by reference. These patents include U.S. Pat. Nos. 5,404,384; 5,533,079; 5,790,409; 5,848,593; 5,912,818; 5,957,372; 5,961,036; 5,971,593; 5,993,046; 6,019,249; 6,073,834; 6,108,588; 6,112,502; 6,141,942; 6,163,737; 6,470,234; and 6,658,322. In addition the disclosures of the following U.S. Patent Applications are incorporated: Ser. Nos. 09/014,076; 09/086,857; 09/288,685; 09/384,650; 09/428,035; 09/428,036; 09/849,625; and 09/921,014.

Thus the foregoing exemplary system and method accomplishes one or more of the above stated objectives, eliminates difficulties encountered in the use of prior systems and methods, solves problems and attains one or more useful results.

Thus the system and method of the present invention achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function, and shall not be limited to the structures shown herein or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations, methods and relationships are set forth in the appended claims.

I claim:

1. Method comprising:
   (a) storing a physician medical order received at a pharmacy as an electronic image;
   (b) displaying at least a portion of the electronic image on a display screen of a pharmacist work station located at a pharmacy, wherein the pharmacist work station includes at least one electronic image annotation tool;
   (c) operating the at least one electronic image annotation tool to provide at least one electronic marking in the electronic image while the portion is displayed on the display screen, wherein the portion with the at least one electronic marking thereon is displayed on the display screen;
   (d) storing the electronic image with the at least one marking as an annotated physician medical order;
   (e) operating the work station to select an electronic image of a physician medical order for display;
   (f) responsive to the selection in (e), automatically displaying on the display screen a zoomed-in defined portion of the selected electronic image;
   wherein the defined portion comprises an electronic image quadrant, wherein the electronic image quadrant is one of a plurality of user-selectable electronic image quadrants, wherein step (f) includes automatically displaying on the display screen a zoomed-in quadrant of the electronic image selected in step (e).

2. The method according to claim 1 wherein step (c) includes operating the at least one electronic image annotation tool to provide an electronic marking comprising at least one of a checkmark, a highlighting, a writing, a drawing, a note with user-added text, and a note with predefined text.

3. The method according to claim 1 wherein step (d) includes storing an electronic image of an annotated physician medical order in a manner that allows an annotation history of a physician medical order to be reviewed at the work station.

4. The method according to claim 1 wherein step (a) includes storing an electronic image of an originally received physician medical order in a first file, wherein step (d) includes storing the at least one electronic marking in a second file, wherein the second file is different from the first file.

5. The method according to claim 1 wherein prior to step (a), adding a verification code to an electronic image of an originally received physician medical order, wherein step (a) includes storing the electronic image with the verification code.

6. The method according to claim 1 and further comprising:
   (g) prior to step (a), receiving at the pharmacy the physician medical order sent from a medical station remotely located from the pharmacy via facsimile transmission;
   (h) sending the annotated physician medical order from the pharmacy to the medical station via facsimile transmission.

7. The method according to claim 1 wherein the work station enables the printing of an annotated physician medical order with or without at least one marking corresponding to the at least one electronic marking, and further comprising:
   (g) operating the work station to select how an annotated physician medical order is to be printed; and
   (h) responsive to step (e), either:
       printing the annotated physician medical order with the at least one marking, or
       printing the annotated physician medical order without the at least one marking.

8. Method comprising:
   (a) storing a physician medical order received at a pharmacy as an electronic image;
   (b) displaying at least a portion of the electronic image on a display screen of a pharmacist work station located at a pharmacy, wherein the pharmacist work station includes at least one electronic image annotation tool;
   (c) operating the at least one electronic image annotation tool to provide at least one electronic marking in the electronic image while the portion is displayed on the display screen, wherein the portion with the at least one electronic marking thereon is displayed on the display screen;
   (d) storing the electronic image with the at least one marking as an annotated physician medical order;
   (e) placing physician medical orders received at the pharmacy into an electronic order prioritizing queue, wherein at least a portion of the queue is displayable on the display screen;
   wherein orders at a top area of the queue have a higher priority than orders at a bottom area of the queue, and further comprising:
   (f) operating the work station to place an order on hold, wherein placing an order on hold temporarily moves the order to a position at the bottom of the queue until a time limit is reached causing the order to be moved to the top of the queue.

9. The method according to claim 8 wherein step (f) includes positioning the order at the bottom of the queue until one of a timeout value and a hold timeout limit is reached causing the order to be moved to the top of the queue, wherein a time period of the hold timeout limit is greater than a time period of the time out value, wherein the time period of the hold timeout limit corresponds to a maximum time that an order can be placed on hold, enabling an order to be placed on hold more than once.

10. Method comprising:
    (a) storing at a pharmacy, an electronic image of a physician medical order,
        wherein the electronic image is stored in a first file as part of an original physician medical order,
        wherein the pharmacy includes a pharmacist work station,
        wherein the pharmacist work station enables the displaying of the original physician medical order;
    (b) displaying the electronic image on a display screen of the pharmacist work station,
        wherein the pharmacist work station includes at least one electronic image annotation tool,
        wherein the at least one electronic image annotation tool is usable to provide at least one electronic marking to the electronic image,
            wherein the at least one electronic marking comprises at least one of a checkmark, a highlighting, a writing, a drawing, a note with user-added text, and a note with predefined text;

(c) using the at least one electronic image annotation tool while the electronic image is being displayed on the display screen, in providing the at least one electronic marking to the electronic image,
wherein the providing causes the electronic image to be displayed on the display screen with the at least one electronic marking thereon;
(d) storing the at least one electronic marking in a second file as part of an annotated physician medical order, wherein the second file is different from the first file;
wherein the annotated physician medical order includes the electronic image with the at least one electronic marking thereon,
wherein the pharmacist work station enables the displaying of the annotated physician medical order;
(e) subsequent to (d), operating the pharmacist work station to select display of either:
(ei) the original physician medical order, or
(eii) the annotated physician medical order; and
(f) responsive at least in part to (e), either:
(fi) displaying the electronic image without the at least one electronic marking thereon responsive to (ei), wherein the first file is displayed, or
(fii) displaying the electronic image with the at least one electronic marking thereon responsive to (eii), wherein the second file is displayed layered over the first file.

11. The method according to claim 10 and further comprising:
(g) placing physician medical orders stored at the pharmacy into an electronic order-prioritizing queue, wherein at least a portion of the Queue is displayable on the display screen; and
(h) displaying at least a portion of the electronic image along with at least a portion of the queue on the same display screen.

12. The method according to claim 10 wherein the pharmacist work station is operative to cause the display screen to display a user interface including annotation tool icons, wherein selection of a displayed annotation tool icon is operative cause selection of a particular electronic image annotation tool corresponding to the displayed icon, and further comprising (g) prior to step (c), selecting a particular electronic image annotation tool via a displayed annotation tool icon.

13. The method according to claim 10
wherein (e) includes operating the pharmacist work station to select display of the annotated physician medical order,
wherein (f) includes displaying the electronic image with the at least one electronic marking thereon, wherein the second file is displayed layered over the first file.

14. The method according to claim 10 wherein step (c) includes operating the at least one electronic image annotation tool to provide an electronic marking comprising a checkmark.

15. The method according to claim 10 wherein step (c) includes operating the at least one electronic image annotation tool to provide an electronic marking comprising a highlighting.

16. The method according to claim 10 wherein step (c) includes operating the at least one electronic image annotation tool to provide an electronic marking comprising a writing.

17. The method according to claim 10 wherein step (c) includes operating the at least one electronic image annotation tool to provide an electronic marking comprising a drawing.

18. The method according to claim 10 wherein step (c) includes operating the at least one electronic image annotation tool to provide an electronic marking comprising a note with user-added text.

19. The method according to claim 10 wherein step (c) includes operating the at least one electronic image annotation tool to provide an electronic marking comprising a note with predefined text.

20. The method according to claim 10 wherein the physician medical order comprises a prescription,
wherein (c) includes annotating the prescription by providing the at least one electronic marking to an electronic image of the prescription while the electronic image of the prescription is being displayed on the display screen,
wherein (fii) includes displaying the annotated prescription by displaying the electronic image of the prescription with the at least one electronic marking thereon.

* * * * *